(12) United States Patent
Shen et al.

(10) Patent No.: US 7,576,122 B2
(45) Date of Patent: Aug. 18, 2009

(54) OPHTHALMIC COMPOSITIONS FOR TREATING OCULAR HYPERTENSION

(75) Inventors: Dong-Ming Shen, Edison, NJ (US); James B. Doherty, Montvale, NJ (US)

(73) Assignee: Merck & Co. Inc., Rahway, NJ (US)

( * ) Notice: Subject to any disclaimer, the term of this patent is extended or adjusted under 35 U.S.C. 154(b) by 339 days.

(21) Appl. No.: 10/570,913

(22) PCT Filed: Aug. 27, 2004

(86) PCT No.: PCT/US2004/027915

§ 371 (c)(1),
(2), (4) Date: Mar. 1, 2003

(87) PCT Pub. No.: WO2005/020917

PCT Pub. Date: Mar. 10, 2005

(65) Prior Publication Data

US 2006/0276504 A1 Dec. 7, 2006

Related U.S. Application Data

(60) Provisional application No. 60/499,628, filed on Sep. 2, 2003.

(51) Int. Cl.
*A61K 31/343* (2006.01)
*A61K 31/381* (2006.01)
*C07D 307/80* (2006.01)
*C07D 333/56* (2006.01)
*C07D 409/02* (2006.01)

(52) U.S. Cl. .................. 514/443; 514/469; 549/58; 549/467

(58) Field of Classification Search ................ 514/443, 514/469; 549/58, 467
See application file for complete search history.

(56) References Cited

U.S. PATENT DOCUMENTS

| 4,690,931 A | 9/1987 | Wick et al. |
| 5,151,444 A | 9/1992 | Ueno et al. |
| 5,296,504 A | 3/1994 | Stjernschantz et al. |
| 5,352,708 A | 10/1994 | Woodward et al. |
| 5,422,368 A | 6/1995 | Stjernschantz et al. |
| 5,573,758 A | 11/1996 | Adorante et al. |
| 5,889,052 A | 3/1999 | Klimko et al. |
| 5,925,342 A | 7/1999 | Adorante et al. |

FOREIGN PATENT DOCUMENTS

| EP | 1114816 | 7/2001 |
| GB | 1286861 | 9/1969 |
| WO | WO 89/10757 | 11/1989 |
| WO | WO 94/13275 | 6/1994 |
| WO | WO 94/28900 | 12/1994 |
| WO | WO 96/33719 | 10/1996 |
| WO | WO 01/46140 | 6/2001 |
| WO | WO 01/70702 | 9/2001 |
| WO | WO 02/24647 | 3/2002 |
| WO | WO 02/42268 | 5/2002 |
| WO | WO 2004/043354 | 5/2004 |
| WO | WO 2004/085431 | 10/2004 |

OTHER PUBLICATIONS

A. M. Harman et al., "Development and Aging of Cell Topography in the Human Retinal Pigment Epithelium", 1997, pp. 2016-2026, vol. 38, No. 10, Investigative Ophthalmology & Visual Science.
E. L. Eliel et al., "Chirality in Molecules Devoid of Chiral Centers", 1994, pp. 1119-1190, Chap. 14, *Stereochemistry of Organic Compounds*.
S. M. Berge et al., "Pharmaceutical Salts", 1977, pp. 1-19, vol. 66, No. 1, J. of Pharmaceutical Sciences.
M. Topolski, "Electrophilic Reactions of Carbenoids. Synthesis of Fused Heterocyclic Systems via Intramolecular Nucleophilic Substitution of Carbenoids", 1995, pp. 5588-5594, vol. 60, J. Org. Chem.
C.F. H. Allen et al., "Thiosalicylic Acid", 1991-2002, pp. 580, Coll. vol. 2, Organic Syntheses.
M. Hanner et al., "The Beta Subunit of the High Conductance Calcium-Activated Potassium Channel", 1998, pp. 16283-169296, vol. 273, No. 26, J. of Biological Chemistry.
A. F. Abdel-Magid et al., "Reductive Amination of Aldehydes and Ketones with Sodium Triacetoxyborohydride. Studies on Direct and Indirect Reductive Amination Procedures", 1996, pp. 3849-3862, vol. 61, J. Org. Chem.
P. M. Vasallo et al., "Expression of Na,K ATPase Alpha Subunit Isoforms in the Human Ciliary Body and Cultured Ciliary Epithelial Cells", 1989, pp. 243-252, vol. 141, J. of Cellular Physiology.
E. Tsuji et al., "Preparation of 3-Acetoacetylaminobenzo[b] Furan Derivatives with Cysteinyl Leukotriene Recptor 2 Antagonistic Activity", 2003, pp. 3139-3141, vol. 1, Org. Biomol. Chem.
G. Dyker et al., "Palladium-Catalyzed C-H Activation oat Methoxy Groups for Cross-Coupling Reactions: A New Approach to Substituted Benzo {b} Furans", 1993, Vol. 58, p. 6426-6428, American Chemical Society.
J. R. Pearson et al., "Vinylindenes and Some Heteroanalogues in the Diels-Alder Reaction. IX 3-Vinylbenzofuran and 1,4-Naphthoquinone", 1991, Vol. 44, p. 907-917, Aust. J. Chem.
S.V. Tolkunov et al., "Recyclization of 1,3-Dimethylbenzo[b]Furn[2,3-c]- and 1,3-Dimethylbenzo {b} Thieno{2,3-c}Pyrlium when Treated with Secondary Amines. Sytnethesis of 3-Dialkylamino Derivatives of Dibenzofuran and Dibenzothiphene", 1998, vol. 34, No. 2, Chemistry of Heterocyclic Compound.

*Primary Examiner*—Taofiq A Solola
(74) *Attorney, Agent, or Firm*—Sylvia A. Ayler; William Krovatin

(57) ABSTRACT

This invention relates to potent potassium channel blocker compounds of Formula I or a formulation thereof for the treatment of glaucoma and other conditions which leads to elevated intraoccular pressure in the eye of a patient. This invention also relates to the use of such compounds to provide a neuroprotective effect to the eye of mammalian species, particularly humans.

13 Claims, No Drawings

OPHTHALMIC COMPOSITIONS FOR TREATING OCULAR HYPERTENSION

This application claims the benefit under 35 U.S.C. 119(e) of U.S. Provisional Application No. 60/499,628 filed Sep. 2, 2003.

BACKGROUND OF THE INVENTION

Glaucoma is a degenerative disease of the eye wherein the intraocular pressure is too high to permit normal eye function. As a result, damage may occur to the optic nerve head and result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by the majority of ophthalmologists to represent merely the earliest phase in the onset of glaucoma.

There are several therapies for treating glaucoma and elevated intraocular pressure, but the efficacy and the side effect profiles of these agents are not ideal. Recently potassium channel blockers were found to reduce intraocular pressure in the eye and therefore provide yet one more approach to the treatment of ocular hypertension and the degenerative ocular conditions related thereto. Blockage of potassium channels can diminish fluid secretion, and under some circumstances, increase smooth muscle contraction and would be expected to lower IOP and have neuroprotective effects in the eye. (see U.S. Pat. Nos. 5,573,758 and 5,925,342; Moore, et al., Invest. Ophthalmol. Vis. Sci 38, 1997; WO 89/10757, WO94/28900, and WO 96/33719).

SUMMARY OF THE INVENTION

This invention relates to the use of potent potassium channel blockers or a formulation thereof in the treatment of glaucoma and other conditions that are related to elevated intraocular pressure in the eye of a patient. This invention also relates to the use of such compounds to provide a neuroprotective effect to the eye of mammalian species, particularly humans. More particularly this invention relates to the treatment of glaucoma and/or ocular hypertension (elevated intraocular pressure) using novel benzofurans, benzothiophenes, and their aza derivatives having the structural formula I:

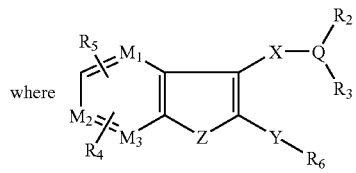

Formula I where or a pharmaceutically acceptable salt, enantiomer, diastereomer or mixture thereof: wherein, R represents hydrogen, or $C_{1-6}$ alkyl;

X represents $-(CHR_7)_p-$, or $-(CHR_7)_p CO-$;

Y represents $-CO(CH_2)_n-$, $(CH_2)_n$, $-CH(OR)-$, $OR_6$, or $SR_6$;

Z=O or S;

M1, M2, and M3 are independently CH or N;

Q represents $CR^y$, N, or O, wherein $R_2$ is absent when Q is O;

$R^y$ represents H, $C_{1-6}$ alkyl, $-(CH_2)_n C_{3-8}$ cycloalkyl, $-(CH_2)_n C_{3-10}$ heterocyclyl, $-(CH_2)_n C_{5-10}$ heteroaryl, or $-(CH_2)_n C_{6-10}$ aryl;

$R_w$ represents H, $C_{1-6}$ alkyl, $-C(O)C_{1-6}$ alkyl, $-C(O)OC_{1-6}$ alkyl, $-SO_2N(R)_2$, $-SO_2C_{1-6}$ alkyl, $-SO_2C_{6-10}$ aryl, $NO_2$, CN or $-C(O)N(R)_2$;

$R_2$ represents hydrogen, $C_{1-10}$ alkyl, OH, $C_{2-6}$ alkenyl, $C_{1-6}$ alkylSR, $-(CH_2)_n O(CH_2)_m OR$, $-(CH_2)_n(CHR_7)_q$ $(CH_2)_m$ $C_{1-6}$ alkoxy, $-(CH_2)_n(CHR_7)_q(CH_2)_m C_{3-8}$ cycloalkyl, $-(CH_2)_n(CHR_7)_q(CH_2)_m C_{3-8}$cycloalkenyl, $-(CH_2)_n(CHR_7)_q(CH_2)_m C_{3-10}$ heterocyclyl, $-N(R)_2$, $-COOR$, or $-(CH_2)_n(CHR_7)_q(CH_2)_m C_{6-10}$ aryl, said alkyl, cycloalkyl, heterocyclyl, or aryl optionally substituted with 1-5 groups selected from $R^a$;

$R_3$ represents hydrogen, $C_{1-10}$ alkyl, $C_{2-6}$ alkenyl, $-(CH_2)_n$ $(CHR_7)_q(CH_2)_m C_{3-8}$ cycloalkyl, $-(CH_2)_n(CHR_7)_q$ $(CH_2)_m$ cycloalkenyl, $-(CH_2)_n(CHR_7)_q(CH_2)_m C_{3-10}$ heterocyclyl, $-(CH_2)_n(CHR_7)_q(CH_2)_m COOR$, $-(CH_2)_n$ $(CHR_7)_q(CH_2)_m C_{6-10}$ aryl, $-(CH_2)_n(CHR_7)_q(CH_2)_m$ $NHR_8$, $-(CH_2)_n(CHR_7)_q(CH_2)_m N(R)_2$, $-(CH_2)_n$ $(CHR_7)_q(CH_2)_m N(R)_3$, $-(CH_2)_n(CHR_7)_q(CH_2)_m N(R_8)_2$, $-(CH_2)_n(CHR_7)_q(CH_2)_m NHCOOR$, $-(CH_2)_n(CHR_7)_q$ $(CH_2)_m N(R_8)CO_2R$, $-(CH_2)_n(CHR_7)_q(CH_2)_m N(R_8)$ COR, $-(CH_2)_n(CHR_7)_q(CH_2)_m NHCOR$, $-(CH_2)_n$ $(CHR_7)_q(CH_2)_m CONH(R_8)$, aryl, $-(CH_2)_n(CHR_7)_q$ $(CH_2)_m C_{1-6}$ alkoxy, $CF_3$, $-(CH_2)_n(CHR_7)_q(CH_2)_m SO_2R$, $-(CH_2)_n(CHR_7)_q(CH_2)_m SO_2N(R)_2$, $-(CH_2)_n(CHR_7)_q$ $(CH_2)_m$ $CON(R)_2$, $-(CH_2)_n(CHR_7)_q(CH_2)_m CONHC$ $(R)_3$, $-(CH_2)_n(CHR_7)_q(CH_2)_m CONHC(R)_2CO_2R$, $-(CH_2)_n(CHR_7)_q(CH_2)_m COR_8$, nitro, cyano or halogen, said alkyl, cycloalkyl, alkoxy, heterocyclyl, or aryl optionally substituted with 1-5 groups of $R^a$;

or, when Q equals $CR^y$ or N, $R_2$ and $R_3$ taken together with the intervening $CR^y$ or N form a 3-10 membered carbocyclic or heterocyclic ring or fused ring optionally interrupted by 1-2 atoms of O, S, C(O) or NR, and optionally having 1-5 double bonds, and optionally substituted by 1-3 groups selected from $R^a$;

$R_4$ and $R_5$ independently represent hydrogen, $C_{1-6}$ alkoxy, OH, $C_{1-6}$ alkyl, $C_{1-6}$ alkyl-S, $C_{1-6}$ alkyl-CO—, $C_{1-6}$ alkenyl, $C_{3-8}$ cycloalkoxy, $C_{3-8}$ cycloalkyl, $C_{3-8}$ cycloalkyl-S, $C_{3-8}$ cycloalkyl-CO—, COOR, $SO_3H$, $-O(CH_2)_n N(R)_2$, $-O(CH_2)_n CO_2R$, $-OPO(OH)_2$, $CF_3$, $-N(R)_2$, nitro, cyano, $C_{1-6}$ alkylamino, or halogen;

$R_6$ represents hydrogen, $C_{1-10}$ alkyl, $-(CH_2)_n(CHR_7)_q$ $(CH_2)_m$ $C_{6-10}$ aryl, $-(CH_2)_n(CHR_7)_q(CH_2)_m C_{5-10}$ heteroaryl, $NR_cR_d$, $-NR-(CH_2)_n(CHR_7)_q(CH_2)_m C_{6-10}$ aryl, $-N-((CH_2)_n(CHR_7)_q(CH_2)_m C_{6-10}$ aryl)$_2$, $-(CH_2)_n$ $(CHR_7)_q(CH_2)_m C_{3-10}$ heterocyclyl, $-NR-$ $(CH_2)_n(CHR_7)_q(CH_2)_m C_{3-10}$ heterocyclyl, $-N-((CH_2)_n$ $(CHR_7)_q(CH_2)_m C_{3-10}$ heterocyclyl)$_2$ $(C_{6-10}$ aryl)$O-$, $-(CH_2)_n(CHR_7)_q(CH_2)_m$ $C_{3-8}$ cycloalkyl, $-COOR$, $-C(O)CO_2R$, said aryl, cycloalkyl, heteroaryl, heterocyclyl and alkyl optionally substituted with 1-3 groups selected from $R^a$;

$R_c$ and $R_d$ independently represent H, C1-6 alkyl, $C_{2-6}$ alkenyl, $-(CH_2)_n C_{6-10}$ aryl, $-(CH_2)_n C_{5-10}$ heteroaryl, $C_{1-6}$ alkylSR, $-(CH_2)_n O(CH_2)_m OR$, $-(CH_2)_n C_{1-6}$ alkoxy, or $-(CH_2)_n C_{3-8}$ cycloalkyl;

or $R_c$ and $R_d$ taken together with the intervening N atom form a 4-10 membered heterocyclic carbon ring optionally interrupted by 1-2 atoms of O, S, C(O) or NR, and optionally having 1-4 double bonds, and optionally substituted by 1-3 groups selected from $R^a$;

$R_7$ represents hydrogen, $C_{1-6}$ alkyl, —$(CH_2)_n$COOR or —$(CH_2)_n$N(R)$_2$, $R_8$ represents —$(CH_2)_n C_{3-8}$ cycloalkyl, —$(CH_2)_{n\ 3-10}$ heterocyclyl, $C_{1-6}$ alkoxy or —$(CH_2)_n C_{5-10}$ heteroaryl, —$(CH_2)_n$ $C_{6-10}$ aryl said cycloalkyl, heterocyclyl, aryl or heteroaryl optionally substituted with 1-3 groups selected from $R^a$;

$R^a$ represents F, Cl, Br, I, $CF_3$, $N(R)_2$, $NO_2$, CN, —$COR_8$, —$CONHR_8$, —$CON(R_8)_2$, —$O(CH_2)_n$COOR, —NH$(CH_2)_n$OR, —COOR, —$OCF_3$, —NHCOR, —$SO_2$R, —$SO_2NR_2$, —SR, $(C_1$-$C_6$ alkyl)O—, —$(CH_2)_n$O$(CH_2)_m$OR, —$(CH_2)_n C_{1-6}$ alkoxy, (aryl)O—, —OH, $(C_1$-$C_6$ alkyl) $S(O)_m$—, $H_2$N—C(NH)—, $(C_1$-$C_6$ alkyl)C(O)—, $(C_1$-$C_6$ alkyl)OC(O)NH—, —$(C_1$-$C_6$ alkyl)NR$_w$(CH$_2$)$_n$ $C_{3-10}$ heterocyclyl-R$_w$, —$(C_1$-$C_6$ alkyl)O(CH$_2$)$_n C_{3-10}$ heterocyclyl-R$_w$, —$(C_1$-$C_6$ alkyl)S(CH$_2$)$_n C_{3-10}$ heterocyclyl-R$_w$, —$(C_1$-$C_6$ alkyl)—$C_{3-10}$ heterocyclyl-R$_w$, —$(CH_2)_n$—$Z^1$—C($=Z^2$)N(R)$_2$, —$(C_{2-6}$ alkenyl)NR$_w$(CH$_2$)$_n C_{3-10}$ heterocyclyl-R$_w$, —$(C_{2-6}$ alkenyl)O(CH$_2$)$_n C_{3-10}$ heterocyclyl-R$_w$, —$(C_{2-6}$ alkenyl)S(CH$_2$)$_n C_{3-10}$ heterocyclyl-R$_w$, —$C_{2-6}$ alkenyl)-$C_{3-10}$ heterocyclyl-R$_w$, —$(C_{2-6}$ alkenyl)-$Z^1$—C($=Z^2$)N(R)$_2$, —$(CH_2)_n$SO$_2$R, —$(CH_2)_n$SO$_3$H, —$(CH_2)_n$PO(OR)$_2$, —$(CH_2)_n$OH, —$(CH_2)_n$(CHR$_7$)$_q$ $(CH_2)_m$OPO(OR)$_2$, $C_{3-10}$cycloalkyl, $C_{6-10}$ aryl, $C_{3-10}$ heterocyclyl, $C_{2-6}$ alkenyl, and $C_1$-$C_{10}$ alkyl, said alkyl, alkenyl, alkoxy, heterocyclyl and aryl optionally substituted with 1-3 groups selected from $C_1$-$C_6$ alkyl, CN, $NO_2$, —$(CH_2)_n$OH, —$(CH_2)_n$OPO(OR)$_2$, CON(R)$_2$ and COOR;

$Z^1$ and $Z^2$ independently represents NR$_w$, O, CH$_2$, or S;

m is 0-3;

n is 0-3;

p is 0-3 and q is 0-1.

This and other aspects of the invention will be realized upon inspection of the invention as a whole.

DETAILED DESCRIPTION OF THE INVENTION

The present invention is directed to novel potassium channel blockers of Formula I. It also relates to a method for decreasing elevated intraocular pressure or treating glaucoma by administration, preferably topical or intra-camaral administration, of a composition containing a potassium channel blocker of Formula I described hereinabove and a pharmaceutically acceptable carrier. Use of a compound of formula I in claim 1 for the manufacture of a medicament for the treatment of ocular hypertension or glaucoma.

One embodiment of this invention is realized when Y is —CO(CH$_2$)$_n$ and all other variables are as originally described. A subembodiment of this invention is realized when n is 0.

One embodiment of this invention is realized when Q is —N— and all other variables are as originally described. A subembodiment of this invention is realized when $R_2$ is $C_{1-10}$ alkyl and $R_3$ is $C_{1-10}$ alkyl and said alkyl optionally substituted with 1 to 3 groups of $R^a$.

Another embodiment is realized when Q equals $CR^y$ or N, and $R_2$ and $R_3$ taken together with the intervening $CR^y$ or N form a 3-10 membered carbocyclic or heterocyclic ring or fused ring optionally interrupted by 1-2 atoms of O, S, C(O) or NR, and optionally having 1-5 double bonds, and optionally substituted by 1-3 groups selected from $R^a$;

Another embodiment of this invention is realized when Y is CH(OR) and all other variables are as originally described.

In another embodiment R$_w$ is selected from H, $C_{1-6}$ alkyl, —C(O)$C_{1-6}$ alkyl and —C(O)N(R)$_2$ and all other variables are as originally described.

In another embodiment X is —(CHR$_7$)$_p$—, p is 1-3 and all other variables are as originally described.

In another embodiment X is —(CHR$_7$)$_p$CO—, p is 1-3 and all other variables are as originally described.

In another embodiment Z is S and all other variables are as originally described.

In another embodiment Z is O and all other variables are as originally described.

In another embodiment one of $R_4$ and $R_5$ is H and the other is $C_{1-6}$ alkoxy, halo or hydrogen.

Another embodiment of this invention is realized when M1, M2, and M3 are CH and all other variables are as originally described.

Another embodiment of this invention is realized when at least one of M1, M2, and M3 is N and the other(s) is CH and all other variables are as originally described.

Still another embodiment of this invention is realized when $R_6$ is $C_{1-6}$ alkyl, $(CH_2)_n C_{6-10}$ aryl, $(CH_2)_n C_{3-10}$ heterocyclyl, NR$_c$R$_d$ or $(CH_2)_n C_{3-8}$ cycloalkyl, said alkyl, aryl, heterocyclyl and cycloalkyl optionally substituted with 1 to 5 groups of $R^a$, and all other variables are as originally described.

Yet another embodiment of this invention is realized when $R_6$ is $(CH_2)_n C_{6-10}$ aryl, NR$_c$R$_d$, or $(CH_2)_n C_{3-10}$ heterocyclyl, said aryl, and heterocyclyl optionally substituted with 1 to 5 groups of $R^a$, and all other variables are as originally described.

Yet another embodiment of this invention is realized when $R_7$ is hydrogen or $C_{1-6}$ alkyl, and all other variables are as originally described.

Still another embodiment of this invention is realized when Y is —CO(CH$_2$)$_n$, Q is —N—, $R_2$ is $C_{1-10}$ alkyl or $C_{1-6}$ alkylOH and $R_3$ is $C_{1-10}$ alkyl and said alkyl optionally substituted with 1 to 5 groups of $R^a$. A sub-embodiment of this invention is realized when n is 0 and Z is O. Another sub-embodiment of this invention is realized when n is 0 and Z is S.

Still another embodiment of this invention is realized when Y is —CO(CH$_2$)$_n$, Q is CR$^y$, $R_2$ is $C_{1-10}$ alkyl or $C_{1-6}$alkylOH and $R_3$ is $C_{1-10}$ alkyl and said alkyl optionally substituted with 1 to 5 groups of $R^a$. A sub-embodiment of this invention is realized when n is 0 and Z is O. Another sub-embodiment of this invention is realized when n is 0 and Z is S.

Still another embodiment of this invention is realized when Y is —CO(CH$_2$)$_n$, Q is O, $R_2$ is absent and $R_3$ is $C_{1-10}$ alkyl and said alkyl optionally substituted with 1 to 5 groups of $R^a$. A subembodiment of this invention is realized when n is 0.

Still another embodiment of this invention is realized when Q is —N—, Y is —CO(CH$_2$)$_n$, n=0, Z is S, and $R_6$ is $C_{1-6}$ alkyl, $(CH_2)_n C_{6-10}$ aryl, $(CH_2)_n C_{5-10}$ heteroaryl, $(CH_2)_n C_{3-10}$ heterocyclyl, NR$_c$R$_d$ or $(CH_2)_n C_{3-8}$ cycloalcyl, said alkyl, aryl, heteroaryl, heterocyclyl and alkyl optionally substituted with 1 to 3 groups of $R^a$. A sub-embodiment of this invention is realized when M1, M2 and M3 are CH, X is —(CHR$_7$)$_p$CO—, p is 1-3, $R_2$ is $C_{1-10}$ alkyl or $C_{1-6}$ alkylOH and $R_3$ is $(CH_2)_n C_{3-10}$ heterocyclyl, said heterocyclyl and alkyl optionally substituted with 1 to 3 groups of $R^a$.

Still another embodiment of this invention is realized when Q is —CRy—, n=0, Z is S, and $R_6$ is $C_{1-6}$ alkyl, $(CH_2)_n C_{6-10}$ aryl, $(CH_2)_n C_{5-10}$ heteroaryl, $(CH_2)_n C_{3-10}$ heterocyclyl, NR$_c$R$_d$ or $(CH_2)_n C_{3-8}$ cycloalkyl, said alkyl, aryl, heteroaryl, heterocyclyl and alkyl optionally substituted with 1 to 3 groups of $R^a$.

Still another embodiment of this invention is realized when Q is —N—, Y is —CO(CH$_2$)$_n$, n=0, Z is O, and $R_6$ is $C_{1-6}$ alkyl, $(CH_2)_n C_{6-10}$ aryl, $(CH_2)_n C_{5-10}$ heteroaryl, $(CH_2)_n C_{3-10}$ heterocyclyl, NR$_c$R$_d$ or $(CH_2)_n C_{3-8}$ cycloalkyl, said alkyl, aryl, heteroaryl, heterocyclyl and alkyl optionally substituted with 1 to 3 groups of $R^a$. A sub-embodiment of this invention is realized when M1, M2 and M3 are CH, X is —(CHR$_7$)$_p$CO—, p is 1-3, R$_2$ is C$_{1-10}$ alkyl or C$_{1-6}$ alkylOH and R$_3$ is (CH$_2$)$_n$C$_{3-10}$ heterocyclyl, said heterocyclyl and alkyl optionally substituted with 1 to 3 groups of $R^a$.

Still another embodiment of this invention is realized when Q is —CRy—, n=0, Z is O, and R$_6$ is C$_{1-6}$ alkyl, (CH$_2$)$_n$C$_{6-10}$ aryl, (CH$_2$)$_n$C$_{5-10}$ heteroaryl, (CH$_2$)$_n$C$_{3-10}$ heterocyclyl, NR$_c$R$_d$ or (CH$_2$)$_n$C$_{3-8}$ cycloalkyl, said alkyl, aryl, heteroaryl, heterocyclyl and alkyl optionally substituted with 1 to 3 groups of $R^a$.

Another embodiment of this invention is realized when there is a free hydroxyl group in the compound of formula I. A subembodiment of this invention is realized when the hydroxyl group is derivatized to give a phosphate group: —OPO(OH)$_2$.

Another embodiment of the instant invention is realized when $R^a$ is selected from F, Cl, Br, I, CF$_3$, N(R)$_2$, NO$_2$, CN, —CONHR$_8$, —CON(R$_8$)$_2$, —O(CH$_2$)$_n$COOR, —NH(CH$_2$)$_n$OR, —COOR, —OCF$_3$, —NHCOR, —SO$_2$R, —SO$_2$NR$_2$, —SR, (C$_1$-C$_6$ alkyl)O—, —(CH$_2$)$_n$O(CH$_2$)$_m$OR, —(CH$_2$)$_n$C$_{1-6}$alkoxy, (aryl)O—, —OH, (C$_1$-C$_6$ alkyl)S(O)$_m$—, H$_2$N—C(NH)—, (C$_1$-C$_6$ alkyl)C(O)—, (C$_1$-C$_6$ alkyl)OC(O)NH—, (CH$_2$)$_n$C$_{3-10}$ heterocyclyl, —(C$_1$-C$_6$ alkyl)NR$_w$(CH$_2$)$_n$ C$_{3-10}$ heterocyclyl-R$_w$, —(CH$_2$)$_n$-Z$^1$—C(=Z$^2$)N(R)$_2$, —(C$_{2-6}$ alkenyl)NR$_w$(CH$_2$)$_n$C$_{3-10}$ heterocyclyl-R$_w$, —(C$_{2-6}$ alkenyl)-Z$^1$—C(=Z$^2$)N(R)$_2$, —(CH$_2$)$_n$SO$_2$R, —(CH$_2$)$_n$ SO$_3$H, —(CH$_2$)$_n$OPO(OR)$_2$, C$_{2-6}$ alkenyl, and C$_1$-C$_{10}$ alkyl, said alkyl, heterocyclyl and alkenyl, optionally substituted with 1-3 groups selected from C$_1$-C$_6$ alkyl, and COOR;

Examples of compounds to be used in this invention are as follows:

N,N-Bibutyl-2-[2-(2,2-dimethylpropanoyl)-5-methoxy-1-benzofuran-3-yl]acetamide,
2-[2(2,2-Dimethylpropanoyl)-5-methoxy-1-benzofuran-3-yl]-N,N-diisobutylacetamide,
N-(Cyclopropylmethyl)-2-[2-(2,2-dimethylpropanoyl)-5-methoxy-1-benzofuran-3-yl]-N-propylacetamide,
N-Cyclohexyl-2-[2-(2,2-dimethylpropanoyl)-5-methoxy-1-benzofuran-3-yl]-N-ethylacetamide,
2-[2-(2,2-Dimethylpropanoyl)-5-methoxy-1-benzofuran-3-yl]-N,N-propylacetamide,
N-Butyl-2-[2-(2,2-dimethylpropanoyl)-5-methoxy-1-benzofuran-3-yl]-N-ethylacetamide,
2-[2-(2,2-Dimethylpropanoyl)-5-methoxy-1-benzofuran-3-yl]-N,N-bis(3-methylbutyl)acetamide,
2-[2-(2,2-Dimethylpropanoyl)-5-methoxy-1-benzofuran-3-yl]-N-ethyl-N-(3-methylbutyl)acetamide,
N-Butyl-2-[2-(2,2-dimethylpropanoyl)-5-methoxy-1-benzofuran-3-yl]-N-propylacetamide,
1-{5-Methoxy-3-[2-(trans-octahydroisoquinolin-2(1H)-yl)-2-oxoethyl]-1-benzofuran-2-yl}-2,2-dimethylpropan-1-one,
1-{5-Methoxy-3-[2-(cis-octahydroisoquinolin-2(1H)-yl)-2-oxoethyl]-1-benzofuran-2-yl}-2,2-dimethylpropan-1-one,
1-(3-{2-[Trans-2,5-dipropylpyrrolidin-1-yl]-2-oxoethyl}-5-methoxy-1-benzofuran-2-yl)-2,2-dimethylpropan-1-one,
1-(3-{2-[Cis-2,5-dipropylpyrrolidin-1-yl]-2-oxoethyl}-5-methoxy-1-benzofuran-2-yl)-2,2-dimethylpropan-1-one,
N-(3,3-Dimethylbutyl)-2-[2-(2,2-dimethylpropanoyl)-5-methoxy-1-benzofuran-3-yl]acetamide,
N-(3,3-Dimethylbutyl)-2-[2-(2,2-dimethylpropanoyl)-5-methoxy-1-benzofuran-3-yl]-N-ethylacetamide,
1-[2-(2,2-Dimethylpropanoyl)-5-methoxy-1-benzofuran-3-yl]-3,3-dimethylbutan-2-one,
2-(2-Benzoyl-5-methoxy-1-benzofuran-3-yl)-N,N-dibutylacetamide,
1-[2-(2,2-Dimethylpropanoyl)-5-methoxy-1-benzofuran-3-yl]-3,3-dimethylpentan-2-one
2-[2-(2,2-dimethylpropanoyl)-5-methoxy-1-benzothien-3-yl]-N,N-di-n-butylacetamide;
2-[2-(2,2-dimethylpropanoyl)-5-methoxy-1-benzothien-3-yl]-N,N-diisobutylacetamide;
N-(cyclopropylmethyl)-2-[2-(2,2-dimethylpropanoyl)-5-methoxy-1-benzothien-3-yl]-N-propylacetamide;
N-cyclohexyl-2-[2-(2,2-dimethylpropanoyl)-5-methoxy-1-benzothien-3-yl]-N-ethylacetamide;
2-[2-(2,2-dimethylpropanoyl)-5-methoxy-1-benzothien-3-yl]-N,N-dipropylacetamide;
N-butyl-2-[2-(2,2-ethylpropanoyl)-5-methoxy-1-benzothien-3-yl]-N-ethylacetamide;
2-[2-(2,2-dimethylpropanoyl)-5-methoxy-1-benzothien-3-yl]-N-ethyl-N-(3-methylbutyl)acetamide;
N-butyl-2-[2-(2,2-dimethylpropanoyl)-5-methoxy-1-benzothien-3-yl]-N-propylacetamide;
2-[2-(2,2-dimethylpropanoyl)-5-methoxy-1-benzothien-3-yl]-N,N-bis(3-methylbutyl)acetamide;
1-{5-methoxy-3-[2-(trans-octahydroisoquinolin-2(1H)-yl)-2-oxoethyl]-1-benzothien-2-yl}-2,2-dimethylpropan-1-one;
1-{5-methoxy-3-[2-(cis-octahydroisoquinolin-2(1H)-yl)-2-oxoethyl]-1-benzothien-2-yl}-2,2-dimethylpropan-1-one;
1-(3-{2-[(trans-2,5-dipropylpyrrolidin-1-yl]-2-oxoethyl}-5-methoxy-1-benzothien-2-yl)-2,2-dimethylpropan-1-one;
1-(3-{2-[(cis-2,5-dipropylpyrrolidin-1-yl]-2-oxoethyl}-5-methoxy-1-benzothien-2-yl)-2,2-dimethylpropan-1-one;
N-(3,3-dimethylbutyl)-2-[2-(2,2-dimethylpropanoyl)-5-methoxy-1-benzothien-3-yl]-N-ethylacetamide;
1-[2-(2,2-Dimethylpropanoyl)-5-methoxy-1-benzothien-3-yl]-3,3-dimethylbutan-2-one;
N-Butyl-2-[2-(2,2-dimethylpropanoyl)-5-methoxy-1-benzofaran-3-yl]-N-methylacetamide;
2-[2-(2,2-Dimethylpropanoyl)-5-methoxy-1-benzofuran-3-yl]-N-methyl-N-(3-methylbutyl)acetamide;
2-[2-(2,2-dimethylpropanoyl)-5-fluoro-1-benzothien-3-yl]-N,N-di-n-butylacetamide;
2-[2-(2,2-dimethylpropanoyl)-5-fluoro-1-benzothien-3-yl]-N,N-diisobutylacetamide;
N-(cyclopropylmethyl)-2-[2-(2,2-dimethylpropanoyl)-5-fluoro-1-benzothien-3-yl]-N-propylacetamide;
N-cyclohexyl-2-[2-(2,2-dimethylpropanoyl)-5-fluoro-1-benzothien-3-yl]-N-ethylacetamide;
2-[2-(2,2-dimethylpropanoyl)-5-fluoro-1-benzothien-3-yl]-N,N-dipropylacetamide;
N-butyl-2-[2-(2,2-dimethylpropanoyl)-5-fluoro-1-benzothien-3-yl]-N-ethylacetamide;
2-[2-(2,2-dimethylpropanoyl)-5-fluoro-1-benzothien-3-yl]-N-ethyl-N-3-methylbutyl)acetamide;
N-butyl-2-[2-(2,2-dimethylpropanoyl)-5-fluoro-1-benzothien-3-yl]-N-propylacetamide;
2-[2-(2,2-dimethylpropanoyl)-5-fluoro-1-benzothien-3-yl]-N,N-bis(3-methylbutyl)acetamide;
1-{5-fluoro-3-[2-(trans-octahydroisoquinolin-2(1H)-yl)-2-oxoethyl]-1-benzothien-2-yl}-2,2-dimethylpropan-1-one;
1-{5-fluoro-3-[2-(cis-octahydroisoquinolin-2(1H)-yl)-2-oxoethyl]-1-benzothien-2-yl}-2,2-dimethylpropan-1-one;
1-(3-{2-[(trans-2,5-dipropylpyrrolidin-1-yl]-2-oxoethyl}-5-fluoro-1-benzothien-2-yl)-2,2-dimethylpropan-1-one;
1-(3-{2-[(cis-2,5-dipropylpyrrolidin-1-yl]-2-oxoethyl}-5-fluoro-1-benzothien-2-yl)-2,2-dimethylpropan-1-one;
N-(3,3-dimethylbutyl)-2-[2-(2,2-dimethylpropanoyl)-5-fluoro-1-benzothien-3-yl]-N-ethylacetamide;

2-[2-(2,2-dimethylpropanoyl)-1-benzothien-3-yl]-N,N-di-n-butylacetamide;
2-[2-(2,2-dimethylpropanoyl)-1-benzothien-3-yl]-N,N-di-isobutylacetamide;
N-(cyclopropylmethyl)-2-[2-(2,2-dimethylpropanoyl)-1-benzothien-3-yl]-N-propylacetamide;
N-cyclohexyl-2-[2-(2,2-dimethylpropanoyl)-1-benzothien-3-yl]-N-ethylacetamide;
2-[2-(2,2-dimethylpropanoyl)-1-benzothien-3-yl]-N,N-dipropylacetamide;
N-butyl-2-[2-(2,2-dimethylpropanoyl)-1-benzothien-3-yl]-N-ethylacetamide;
2-[2-(2,2-dimethylpropanoyl)-1-benzothien-3-yl]-N-ethyl-N-(3-methylbutyl)acetamide;
N-butyl-2-[2-(2,2-dimethylpropanoyl)-1-benzothien-3-yl]-N-propylacetamide;
2-[2-(2,2-dimethylpropanoyl)-1-benzothien-3-yl]-N,N-bis(3-methylbutyl)acetamide;
1-{3-[2-(trans-octahydroisoquinolin-2(1H)-yl)-2-oxoethyl]-1-benzothien-2-yl}-2,2-dimethylpropan-1-one;
1-{3-[2-(cis-octahydroisoquinolin-2(1H)-yl)-2-oxoethyl]-1-benzothien-2-yl}-2,2-dimethylpropan-1-one;
1-(3-{2-[(trans-2,5-dipropylpyrrolidin-1-yl]-2-oxoethyl}-1-benzothien-2-yl)-2,2-dimethylpropan-1-one;
1-(3-{2-[(cis-2,5-dipropylpyrrolidin-1-yl]-2-oxoethyl}-1-benzothien-2-yl)-2,2-dimethylpropan-1-one;
N-(3,3-dimethylbutyl)-2-[2-(2,2-dimethylpropanoyl)-1-benzothien-3-yl]-N-ethylacetamide;

or a pharmaceutically acceptable salt, enantiomer, diastereomer or mixture thereof.

The invention is described herein in detail using the terms defined below unless otherwise specified.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Stereochemistry of Carbon Compounds* (John Wiley and Sons, New York 1994), in particular pages 1119-1190)

When any variable (e.g. aryl, heterocycle, $R^1$, $R^6$ etc.) occurs more than one time in any constituent, its definition on each occurrence is independent at every other occurrence. Also, combinations of substituents/or variables are permissible only if such combinations result in stable compounds.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopropyl cyclopentyl and cyclohexyl. When the alkyl group is said to be substituted with an alkyl group, this is used interchangeably with "branched alkyl group".

Cycloalkyl is a cyclic specie of alkyl containing from 3 to 15 carbon atoms, unless otherwise defined, without alternating or resonating double bonds between carbon atoms. It may contain from 1 to 4 rings, which are fused. Examples of such cycloalkyl elements include, but are not limited to, cyclopropyl, cyclobutyl, cyclopentyl, cyclohexyl and cycloheptyl.

Alkenyl is $C_2$-$C_6$ alkenyl.

Alkoxy refers to an alkyl group of indicated number of carbon atoms attached through an oxygen bridge, with the alkyl group optionally substituted as described herein. Said groups are those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

Halogen (halo) refers to chlorine, fluorine, iodine or bromine.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Examples of aryl groups are phenyl, naphthyl, tetrahydronaphthyl, indanyl, biphenyl, phenanthryl, anthryl or acenaphthyl and phenanthrenyl, preferably phenyl, naphthyl or phenanthrenyl. Aryl groups may likewise be substituted as defined. Preferred substituted aryls include phenyl and naphthyl.

The term heterocyclyl or heterocyclic, as used herein, represents a stable 3- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defmed heterocyclic rings is fused to a benzene ring. The heterocyclic ring may be attached at any heteroatom or carbon atom which results in the creation of a stable structure. A fused heterocyclic ring system may include carbocyclic rings and need include only one heterocyclic ring. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, dihydropyrrolyl, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. Preferably, heterocycle is selected from 2-azepinonyl, benzimidazolyl, 2-diazapinonyl, dihydroimidazolyl, dihydropyrrolyl, imidazolyl, 2-imidazolidinonyl, indolyl, isoquinolinyl, morpholinyl, piperidyl, piperazinyl, pyridyl, pyrrolidinyl, 2-piperidinonyl, 2-pyrimidinonyl, 2-pyrollidinonyl, quinolinyl, tetrahydrofuryl, tetrahydroisoquinolinyl, and thienyl.

The term "heteroatom" means O, S or N, selected on an independent basis.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, thienyl and triazolyl. Additional nitrogen atoms may be present together with the first nitrogen and oxygen or sulfur, giving, e.g., thiadiazole.

This invention is also concerned with compositions and methods of treating ocular hypertension or glaucoma by administering to a patient in need thereof one of the compounds of formula I alone or in combination with one or more of the following active ingredients, in combination with a β-adrenergic blocking agent such as timolol, betaxolol, levobetaxolol, carteolol, levobunolol, a parasympathomimetic agent such as epinephrine, iopidine, brimonidine, clonidine, para-aminoclonidine, carbonic anhydrase inhibitor such as dorzolamide, acetazolamide, metazolamide or brinzolamide, an EP4 agonist (such as those disclosed in WO 02/24647, WO 02/42268, EP 1114816, WO 01/46140, PCT Appln. No. CA2004000471, and WO 01/72268), a prostaglandin such as latanoprost, travaprost, unoprostone, rescula, S1033 (compounds set forth in U.S. Pat. Nos. 5,889,052; 5,296,504; 5,422,368; and 5,151,444); a hypotensive lipid such as lumigan and the compounds set forth in U.S. Pat. No. 5,352,708; a neuroprotectant disclosed in U.S. Pat. No. 4,690,931, particularly eliprodil and R-eliprodil as set forth in WO 94/13275, including memantine; an agonist of 5-HT2 receptors as set forth in PCT/US00/31247, particularly 1-(2-aminopropyl)-3-methyl-1H-imdazol-6-ol fumarate and 2-(3-chloro-6-methoxy-indazol-1-yl)-1-methyl-ethylamine or a mixture thereof. An example of a hypotensive lipid (the carboxylic acid group on the α-chain link of the basic prostaglandin structure is replaced with electrochemically neutral substituents) is that in which the carboxylic acid group is replaced with a $C_{1-6}$ alkoxy group such as $OCH_3$ ($PGF_{2\alpha}$ 1-$OCH_3$), or a hydroxy group ($PGF_{2\alpha}$ 1-OH).

Preferred potassium channel blockers are calcium activated potassium channel blockers. More preferred potassium channel blockers are high conductance, calcium activated potassium (Maxi-K) channel blockers. Maxi-K channels are a family of ion channels that are prevalent in neuronal, smooth muscle and epithelial tissues and which are gated by membrane potential and intracellular $Ca^{2+}$.

The present invention is based upon the finding that maxi-K channels, if blocked, inhibit aqueous humor production by inhibiting net solute and $H_2O$ efflux and therefore lower IOP. This finding suggests that maxi-K channel blockers are useful for treating other ophthamological dysfunctions such as macular edema and macular degeneration. It is known that lowering IOP promotes blood flow to the retina and optic nerve. Accordingly, the compounds of this invention are useful for treating macular edema and/or macular degeneration. Use of a compound of formula I in claim 1 for the manufacture of a medicament for the treatment of macular edema and/or macular degeneration It is believed that maxi-K channel blockers which lower IOP are useful for providing a neuroprotective effect. They are also believed to be effective for increasing retinal and optic nerve head blood velocity and increasing retinal and optic nerve oxygen by lowering IOP, which when coupled together benefits optic nerve health. As a result, this invention further relates to a method for increasing retinal and optic nerve head blood velocity, increasing retinal and optic nerve oxygen tension as well as providing a neuroprotective effect or a combination thereof. Use of a compound of formula I in claim 1 for the manufacture of a medicament for increasing retinal and optic nerve head blood velocity, retinal and optic nerve oxygen tension and providing a neuroprotective effect.

A number of marketed drugs function as potassium channel antagonists. The most important of these include the compounds Glyburide, Glipizide and Tolbutamide. These potassium channel antagonists are useful as antidiabetic agents. The compounds of this invention may be combined with one or more of these compounds to treat diabetes. Use of a compound of formula I in claim 1 for the manufacture of a medicament for the treatment of diabetes.

Potassium channel antagonists are also utilized as Class 3 antiarrhythmic agents and to treat acute infarctions in humans. A number of naturally occuring toxins are known to block potassium channels including Apamin, Iberiotoxin, Charybdotoxin, Noxiustoxin, Kaliotoxin, Dendrotoxin(s), mast cell degranuating (MCD) peptide, and β-Bungarotoxin (β-BTX). The compounds of this invention may be combined with one or more of these compounds to treat arrhythmias. Use of a compound of formula I in claim 1 in combination with these compounds for the manufacture of a medicament for the treatment of arrhythmias Depression is related to a decrease in neurotransmitter release. Current treatments of depression include blockers of neurotransmitter uptake, and inhibitors of enzymes involved in neurotransmitter degradation which act to prolong the lifetime of neurotransmitters.

Alzheimer's disease is also characterized by a diminished neurotransmitter release. Three classes of drugs are being investigated for the treatment of Alzheimer's disease cholinergic potentiators such as the anticholinesterase drugs (e.g., physostigmine (eserine), and Tacrine (tetrahydroaminocridine)); nootropics that affect neuron metabolism with little effect elsewhere (e.g., Piracetam, Oxiracetam; and those drugs that affect brain vasculature such as a mixture of ergoloid mesylates amd calcium channel blocking drugs including Nimodipine. Selegiline, a monoamine oxidase B inhibitor which increases brain dopamine and norepinephrine has reportedly caused mild improvement in some Alzheimer's patients. Aluminum chelating agents have been of interest to those who believe Alzheimer's disease is due to aluminum toxicity. Drugs that affect behavior, including neuroleptics, and anxiolytics have been employed. Anxiolytics, which are mild tranquilizers, are less effective than neuroleptics The present invention is related to novel compounds which are useful as potassium channel antagonists. Use of a compound of formula I in claim 1 for the manufacture of a medicament for the treatment of depression and Alzheimer's disease.

The compounds of this invention may be combined with anticholinesterase drugs such as physostigmine (eserine) and Tacrine (tetrahydroaminocridine), nootropics such as Piracetam, Oxiracetam, ergoloid mesylates, selective calcium channel blockers such as Nimodipine, or monoamine oxidase B inhibitors such as Selegiline, in the treatment of Alzheimer's disease. The compounds of this invention may also be combined with Apamin, Iberiotoxin, Charybdotoxin, Noxiustoxin, Kaliotoxin, Dendrotoxin(s), mast cell degranuating (MCD) peptide, β-Bungarotoxin (β-BTX) or a combination thereof in treating arrhythmias. The compounds of this invention may further be combined with Glyburide, Glipizide, Tolbutamide or a combination thereof to treat diabetes.

The herein examples illustrate but do not limit the claimed invention. Each of the claimed compounds are potassium channel antagonists and are thus useful in the described neurological disorders in which it is desirable to maintain the cell in a depolarized state to achieve maximal neurotransmitter release. The compounds produced in the present invention are readily combined with suitable and known pharmaceutically acceptable excipients to produce compositions which may be administered to mammals, including humans, to achieve effective potassium channel blockage.

For use in medicine, the salts of the compounds of formula I will be pharmaceutically acceptable salts. Other salts may, however, be useful in the preparation of the compounds according to the invention or of their pharmaceutically acceptable salts. When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-dimethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, sex and response of the individual patient, as well as the severity of the patient's symptoms.

The maxi-K channel blockers used can be administered in a therapeutically effective amount intravaneously, subcutaneously, topically, transdermally, parenterally or any other method known to those skilled in the art.

Ophthalmic pharmaceutical compositions are preferably adapted for topical administration to the eye in the form of solutions, suspensions, ointments, creams or as a solid insert. Ophthalmic formulations of this compound may contain from 0.01 ppm to 1% and especially 0.1 ppm to 1% of medicament. Higher dosages as, for example, about 10% or lower dosages can be employed provided the dose is effective in reducing intraocular pressure, treating glaucoma, increasing blood flow velocity or oxygen tension. For a single dose, from between 0.1 ng to 5000 ug, preferably 1 ng to 500 ug, and especially 10 ng to 100 ug of the compound can be applied to the human eye.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethyl-cellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a microparticle formulation. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyactylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

Suitable subjects for the administration of the formulation of the present invention include primates, man and other animals, particularly man and domesticated animals such as cats and dogs.

The pharmaceutical preparation may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

The ophthalmic solution or suspension may be administered as often as necessary to maintain an acceptable IOP level in the eye. It is contemplated that administration to the mamalian eye will be about once or twice daily.

For topical ocular administration the novel formulations of this invention may take the form of solutions, gels, ointments, suspensions or solid inserts, formulated so that a unit dosage comprises a therapeutically effective amount of the active component or some multiple thereof in the case of a combination therapy.

The following examples, given by way of illustration, are demonstrative of the present invention.

Definitions of the Terms Used in the Examples are as Follows:
SM—Starting material,
DMSO—dimethyl sulfoxide,
TLC—thin layer chromatography,
SGC—silica gel chromatography,
h=hr=hour,
TBF—tetrahydrofuran,
DMF—dimethylformamide,
LDA—lithium diisopropylamide,
HOBt—1-hydroxybenzotriazole hydrate
EDC—1(3-Dimethylaminopropyl)-3-ethylcarbodiimide hydrochloride
NMR—nuclear magnetic resonance,
TFA—trifluoroacetic acid,
DIEA—N,N-diisopropylethylamine
min—minute,
LC/MS—liquid chromatography/mass spectrometry,
HPLC—high performance liquid chromatography,
equiv=eq=equivalent, General Experimental Conditions: NMR spectra were recorded at room temperature on Varian Instruments referenced to residual solvent peak. LC-MS were measured on an Aglient HPLC and Micromass ZQ detector with electrospray ionization using a 2.0×50 mm X-Terra C18 column and 10–98% MeCN gradient over 3.75 minutes followed by 98% MeCN for 1 minute. The aqueous and MeCN eluents contained 0.06 and 0.05% (v/v) trifluoroacetic acid, respectively. Mass peaks are listed in decreasing order of relative abundance. Preparative HPLC separations were done using a C18 column such as YMC 20×150 mm 5 μ ProC18 column or a 9.4×250 mm SB-C18 Zorbax column.

The compounds of this invention can be made, with modification where appropriate, in accordance with Schemes 1-8.

Scheme 1 illustrates a method for preparing one of two common intermediates, benzofuran 4. When the commercially available hydroxyacetophenone 1 was treated with stoichiometric amounts of 1-bromopinacolone and cesium carbonate at room temperature, analysis indicated that the only product was the ether 2 (Method A). When a slight excess of cesium carbonate was employed in the reaction, the product was a mixture of two diastereomers of 3 plus benzofuran 4 (Method B). The intermediate 3 can be converted to 4 in high yields with catalytic amount of cesium carbonate at slightly elevated temperature. This two-step conversion of 1 to 4 can be simplified by conducting the reaction at elevated temperature with a slight excess of cesium carbonate (Method C).

SCHEME 1

Method A

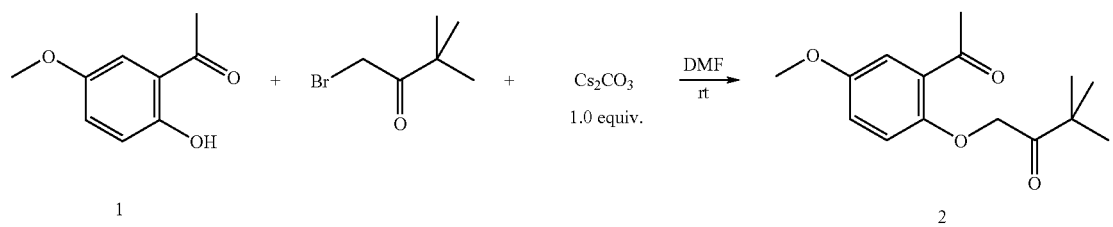

Method B

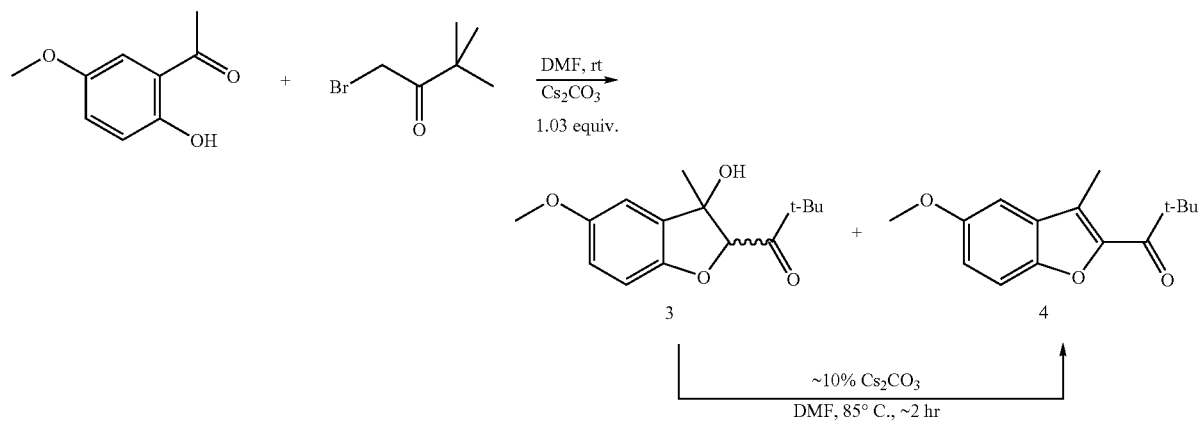

Method C

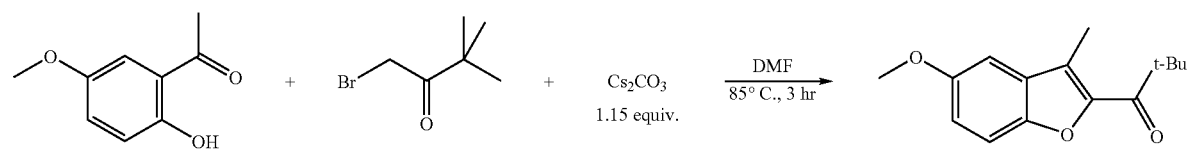

Scheme 2 illustrates the preparation of a second common intermediate, acid 5. The benzofuran 4 can be carboxylated by treatment with a strong base such as LDA followed by carbon dioxide to give acid 5.

SCHEME 2

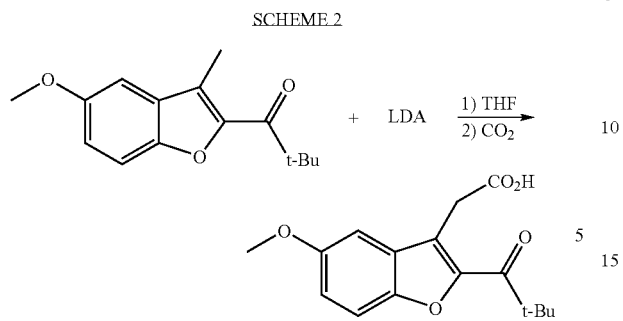

Some compounds of the present invention can be prepared as illustrated in Scheme 3. Many coupling conditions could give amides 6 as the final product. It is usually accompanied by side-product 7. Heating the side-product with amine can give the desired amide also. This side-product can be produced by omitting the dialkyl amine during the coupling reaction. Therefore, the sequence 5-7-6 is an alternative route for the preparation of the compounds of this invention.

SCHEME 3

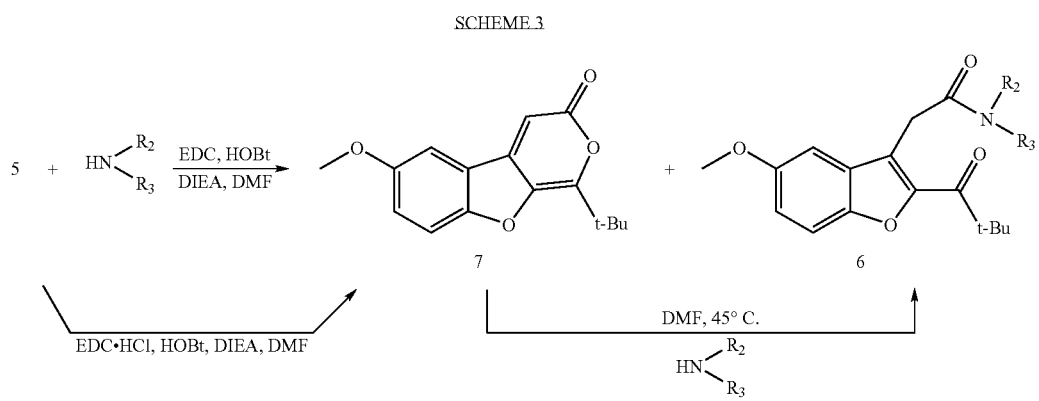

The preparation of another type of compounds of this invention is illustrated in Scheme 4. Quenching the homo-enolate from 4 with trimethyl acetaldehyde gave a mixture of two hydroxyketones 8 and 9. Their oxidation affords diketone 10 as illustrated by the conversion of 8 to 10.

SCHEME 4

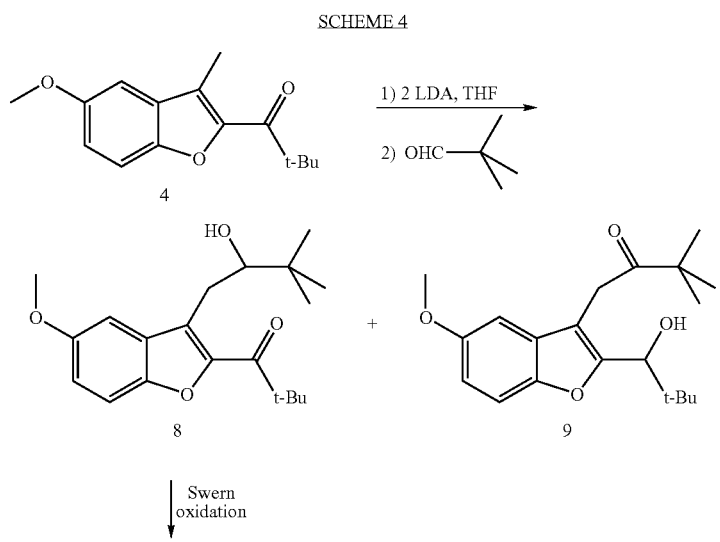

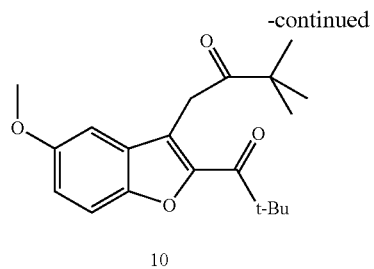
10
SCHEME 5
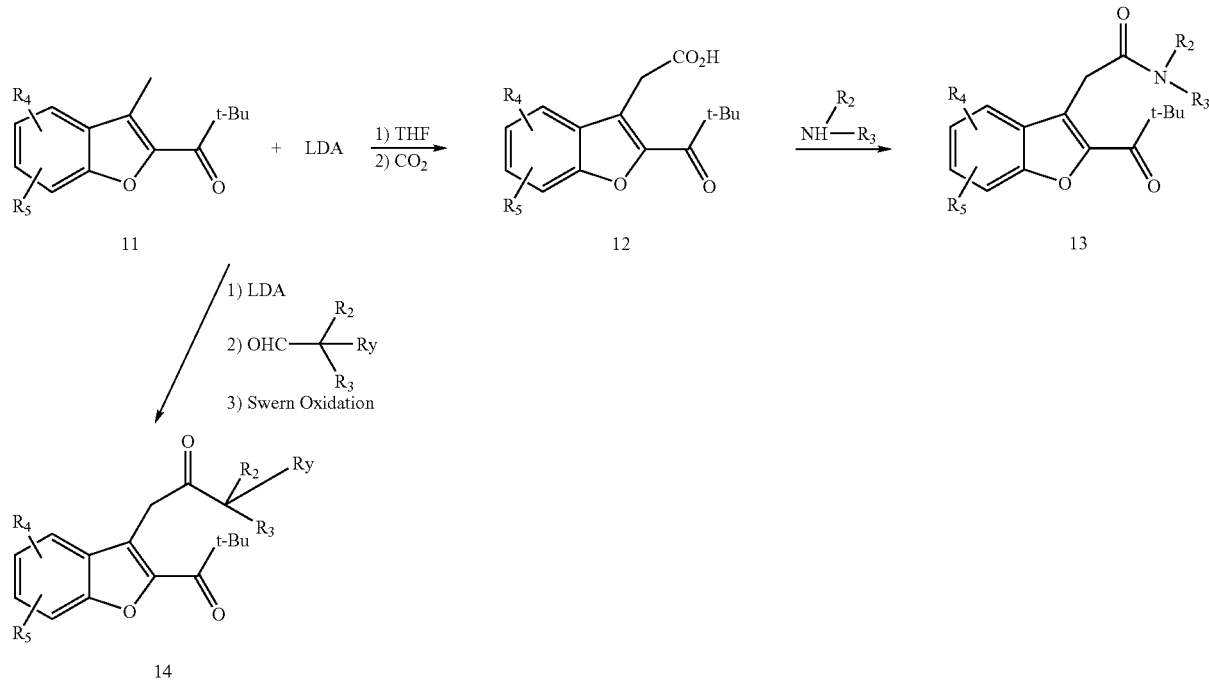
Similarly, substituted analogues such as 11 can be transformed to 13 and 14 using analogous methods. Higher homologues of 1 could be reacted in the same fashion to give desired products 18 and 19 when R7 is not hydrogen (Scheme 6).
SCHEME 6
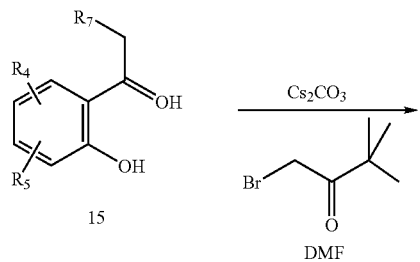

-continued
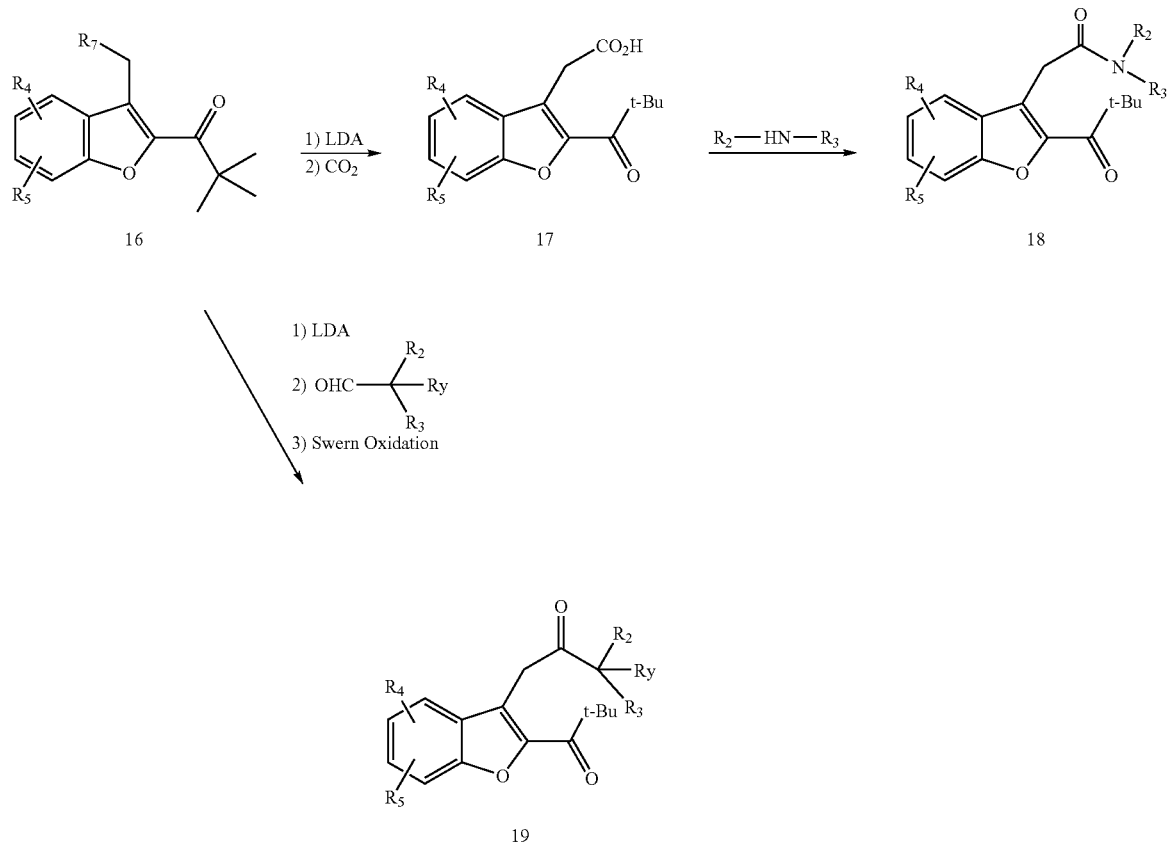
SCHEME 7
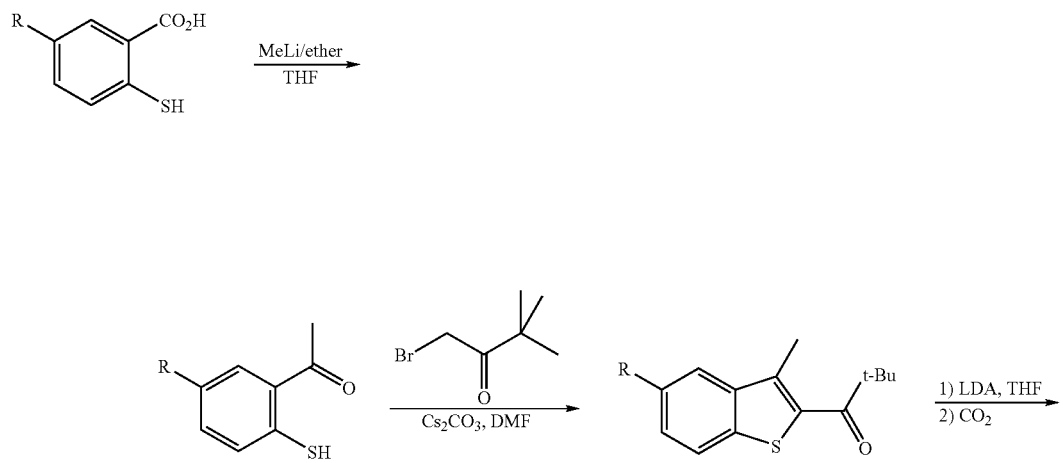

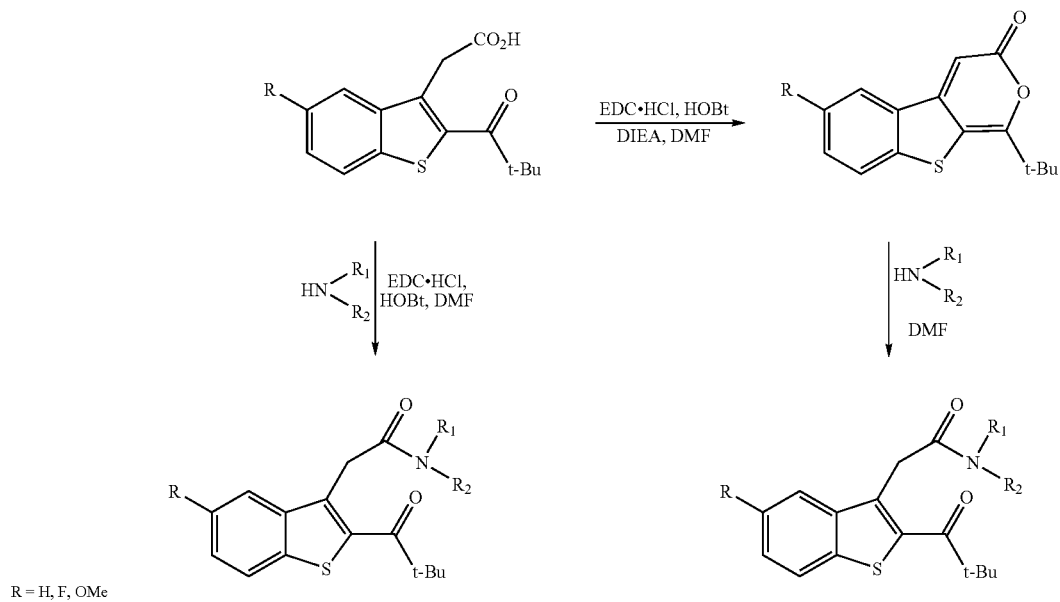

R = H, F, OMe

Scheme 7 shows the preparation of amides in the benzothiophene class. The starting 2-mercaptobenzoic acid is either commercially available or prepared based a literature method (C. F. H. Allen and D. D. MacKay *Org. Syn.* Coll Vol II, 580). Treatment of 2-mercaptobenzoic acid with excess methyl lithium provided the methyl ketone (Topolshi, *J. Org. Chem.* 1995, 60, 5585). This was cyclized with α-bromoketone to give benzothiophene in one step using a new procedure. Carboxylation gives the acetic acid derivative and the subsequence conversion to amides are uneventful.

SCHEME 8

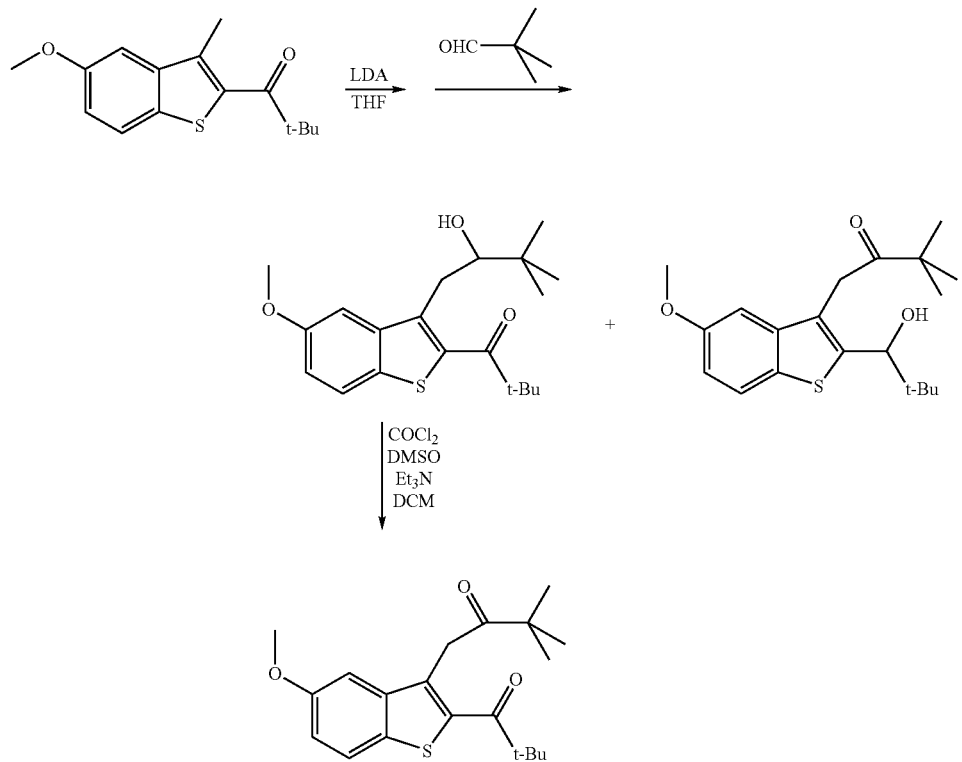

Scheme 8 illustrates the synthesis of ketones in the benzothiophene class. A homoaldol reaction between the 3-methyl benzothiophene from Scheme 7 and an aldehyde provided the alcohol precursor to the ketone and an isomeric alcohol. The alcohol intermediate was oxidized to give the ketone using the Swern oxidation.

EXAMPLE 1

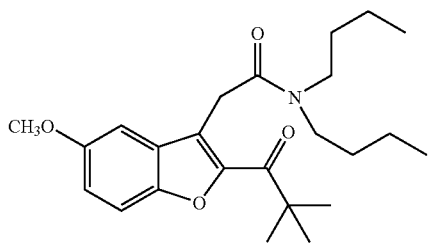

N,N-Bibutyl-2-[2-(2,2-ethylpropanoyl)-5-methoxy-1-benzofuran-3-yl]acetamide

Step A: 1-(5-Methoxy-3-methyl-1-benzofuran-2-yl)-2,2-dimethylpropan-1-one

DMF (4 mL) was added to a mixture of 166 mg 1-(2-hydroxy-5-methoxyphenyl)ethanone and 370 mg cesium carbonate followed by 188 mg 1-bromopinacolone. After heating this mixture in an 85° C. oil bath for 3 hours, it was poured into cold water and extracted with ether. The combined ether extract was washed with water, 1.5 N NaOH, water, and saturated brine, dried over anhydrous $Na_2SO_4$, and concentrated under reduced pressure to give a crude product. It was purified on silica gel (9:1 hexanes and EtOAc) to give the title compound as a colorless solid. $^1$H NMR ($CDCl_3$, 500 MHz) δ 7.41 (d, J=9.0 Hz, 1H), 7.11 (dd, J=2.5 & 9.0 Hz, 1H), 7.04 (d, J=2.5 Hz, 1H), 3.90 (s, 3H), 2.59 (s, 3H), 1.43 (s, 9H).

Step B: [2-(2,2-Dimethylpropanoyl)-5-methoxy-1-benzofuran-3-yl]acetic acid

To a solution of 1.23 g 1-(5-methoxy-3-methyl-1-benzofuran-2-yl)-2,2-dimethylpropan-1-one prepared as described in Step A above in 50 mL anhydrous THF at −78° C. was added 5.0 mL 2.0 M LDA in a mixture of heptane, THF, and ethylbenzene. After stirring for 15 minutes, carbon dioxide gas was bubbled into the reaction mixture for 5 minutes. The cooling bath was removed and the reaction mixture was allowed to warm up to room temperature. It was concentrated under reduced pressure to remove solvents. The residue was diluted with ether and extracted with 0.1 M NaOH (3×). The combine aqueous extract was washed with ether, acidified with concentrated HCl to pH ~1, and extracted with ether. The combined ether extract was washed with saturated brine, dried over anhydrous $Na_2SO_4$, and evaporated to give title compound as colorless solid. $^1$H NMR ($CDCl_3$, 500 MHz) δ 7.47 (d, 9.0 Hz, 1H), 7.18 (dd, 2.5 & 9.2 Hz, 1H), 7.12 (d, 2.5 Hz, 1H), 4.05 (s, 2H), 3.91 (s, 3H), 1.46 (s, 9H). LC-MS: 3.54 min. (m/Z=245.1, 273.1, 291).

Step C: N,N-Bibutyl-2-[2-(2,2-dimethylpropanoyl)-5-methoxy-1-benzofuran-3-yl]acetamide Dissolve a mixture of 17 mg [2-(2,2-dimethylpropanoyl)-5-methoxy-1-benzofuran-3-yl]acetic acid from the Step B above and 18.5 mg HOBt in 1 mL dry DMF. Add 14.9 μL di-n-butylamine followed by 23.0 mg EDC and 35 μL DIEA. This solution was heated at 40° C. for 2 hours. It was purified directly on RP-HPLC using 65-100% MeCN gradient. The fractions containing pure product were pooled and lyophilized to give the title compound. LC-MS: 4.46 min. (m/Z=318.2, 402.2, 424.2).

EXAMPLE 2

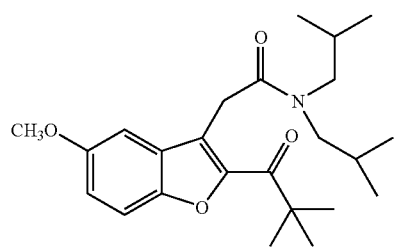

2-[2-(2,2-Dimethylpropanoyl)-5-methoxy-1-benzofuran-3-yl]-N,N-diisobutylacetamide Dissolve a mixture of 17 mg [2-(2,2-dimethylpropanoyl)-5-methoxy-1-benzofuran-3-yl]acetic acid from the Step B Example 1 and 18.5 mg HOBt in 1 mL dry DMF. Add 15.4 μL di-i-butylamine followed by 23.0 mg EDC and 35 μL DIEA. This solution was heated at 40° C. for 2 hours. It was purified directly on RP-HPLC using 65-100% MeCN gradient. The fractions containing pure product were pooled and lyophilized to give the title compound. LC-MS: 4.42 min. (m/Z=318.2, 402.2, 424.2).

EXAMPLE 3

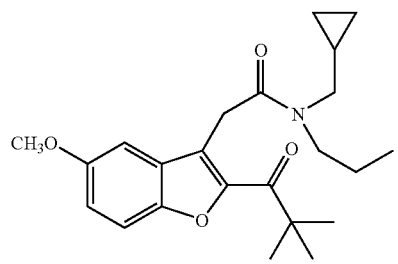

N-(Cyclopropylmethyl)-2-[2-(2,2-dimethylpropanoyl)-5-methoxy-1-benzofuran-3-yl]-N-propylacetamide Dissolve a mixture of 17 mg [2-(2,2-dimethylpropanoyl)-5-methoxy-1-benzofuran-3-yl]acetic acid from the Step B Example 1 and 18.5 mg HOBt in 1 mL dry DMF. Add 12.6 μL N-propylcyclopropanemethylamine followed by 23.0 mg EDC and 35 μL DIEA. This solution was heated at 40° C. for 2 hours. It was purified directly on RP-HPLC using 60-100% MeCN gradient. The fractions containing pure product were pooled and lyophilized to give the title compound. LC-MS: 4.17 min. (m/Z=386.2, 302.1, 408.1).

EXAMPLE 4

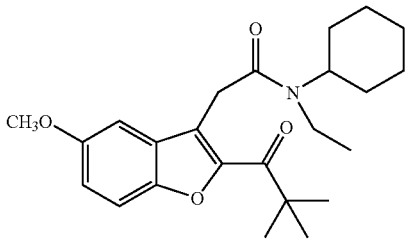

N-Cyclohexyl-2-[2-(2,2-dimethylpropanoyl)-5-methoxy-1-benzofuran-3-yl]-N-ethylacetamide Dissolve a mixture of 17 mg [2-(2,2-dimethylpropanoyl)-5-methoxy-1-benzofuran-3-yl]acetic acid from the Step B Example 1 and 18.5 mg HOBt in 1 mL dry DMF. Add 13.2 μL N-ethylcyclohexylamine followed by 23.0 mg EDC and 35 μL DIEA. This solution was heated at 40° C. for 2 hours. It was purified directly on RP-HPLC using 65-100% MeCN gradient. The fractions containing pure product were pooled and lyophilized to give the title compound. LC-MS: 4.34 min. (m/Z=400.2, 422.1, 316.1).

EXAMPLE 5

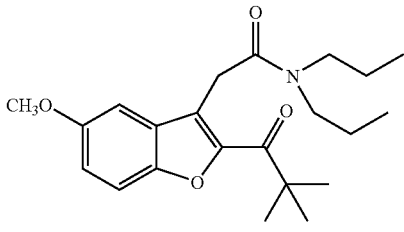

2-[2-(2,2-Dimethylpropanoyl)-5-methoxy-1-benzofuran-3-yl]-N,N-dipropylacetamide

Dissolve a mixture of 17 mg [2-(2,2-dimethylpropanoyl)-5-methoxy-1-benzofuran-3-yl]acetic acid from the Step B Example 1 and 18.5 mg HOBt in 1 mL dry DMF. Add 12.1 μL dipropylamine followed by 23.0 mg EDC and 35 μL DIEA. This solution was heated at 40° C. for 2 hours. It was purified directly on RP-HPLC using 60-100% MeCN gradient. The fractions containing pure product were pooled and lyophilized to give the title compound. LC-MS: 4.16 min. (m/Z=290.1, 374.2, 396.1).

EXAMPLE 6

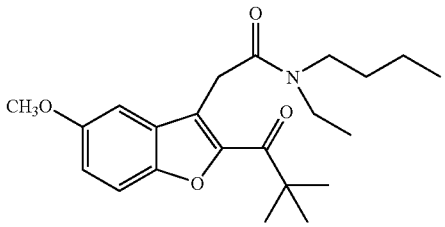

N-Butyl-2-[2-(2,2-dimethylpropanoyl)-5-methoxy-1-benzofuran-3-yl]-N-ethylacetamide Dissolve a mixture of 17 mg [2-(2,2-dimethylpropanoyl)-5-methoxy-1-benzofuran-3-yl]acetic acid from the Step B Example 1 and 18.5 mg HOBt in 1 mL dry DMF. Add 12.0 μL N-ethylbutylamine followed by 23.0 mg EDC and 35 μL DIEA. This solution was heated at 40° C. for 2 hours. It was purified directly on RP-HPLC using 60-100% MeCN gradient. The fractions containing pure product were pooled and lyophilized to give the title compound. LC-MS: 4.15 min. (m/Z=290.1, 374.2, 396.1).

EXAMPLE 7

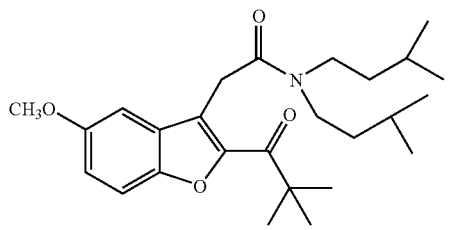

2-[2-(2,2-Dimethylpropanoyl)-5-methoxy-1-benzofuran-3-yl]-N,N-bis(3-methylbutyl)acetamide Dissolve a mixture of 17 mg [2-(2,2-dimethylpropanoyl)-5-methoxy-1-benzofuran-3-yl]acetic acid from the Step B Example 1 and 18.5 mg HOBt in 1 mL dry DMF. Add 18.0 μL di-iso-amylamine followed by 23.0 mg EDC and 35 μL DIEA. This solution was heated at 40° C. for 2 hours. It was purified directly on RP-HPLC using 70-100% MeCN gradient. The fractions containing pure product were pooled and lyophilized to give the title compound. LC-MS: 4.67 min. (m/Z=430.4, 346.2, 452.2).

EXAMPLE 8

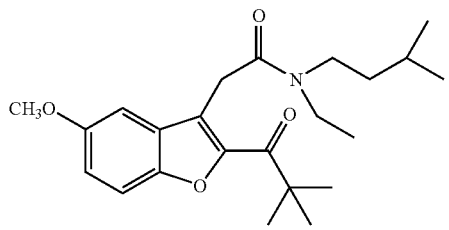

2-[2-(2,2-Dimethylpropanoyl)-5-methoxy-1-benzofuran-3-yl]-N-ethyl-N-(3-methylbutyl)acetamide Dissolve a mixture of 17 mg [2-(2,2-dimethylpropanoyl)-5-methoxy-1-benzofuran-3-yl]acetic acid from the Step B Example 1 and 18.5 mg HOBt in 1 mL dry DMF. Add 10.1 mg N-ethyl-iso-amylamine followed by 23.0 mg EDC and 35 μL DIEA. This solution was heated at 40° C. for 2 hours. It was purified directly on RP-HPLC using 65-100% MeCN gradient. The fractions containing pure product were pooled and lyophilized to give the title compound. LC-MS: 4.29 min. (m/Z=304.2, 388.2, 410.2).

EXAMPLE 9

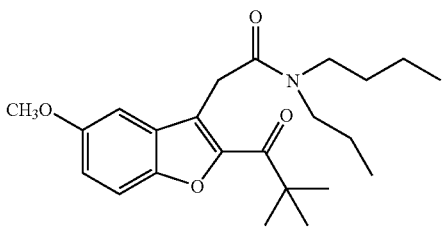

N-Butyl-2-[2-(2,2-dimethylpropanoyl)-5-methoxy-1-benzofuran-3-yl]-N-propylacetamide Dissolve a mixture of 17 mg [2-(2,2-dimethylpropanoyl)-5-methoxy-1-benzofuran-3-yl]acetic acid from the Step B Example 1 and 18.5 mg HOBt in 1 mL dry DMF. Add 13.6 µL N-propylbutylamine followed by 23.0 mg EDC and 35 µL DIEA. This solution was heated at 40° C. for 2 hours. It was purified directly on RP-HPLC using 65-100% MeCN gradient. The fractions containing pure product were pooled and lyophilized to give the title compound. LC-MS: 4.31 min. (m/Z=304.2, 388.2, 410.2).

EXAMPLE 10

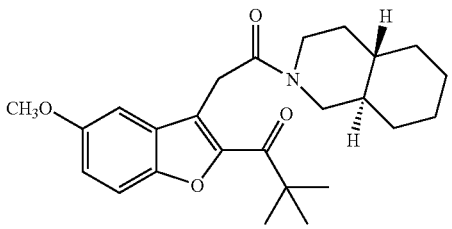

1-{5-Methoxy-3-[2-(trans-octahydroisoquinolin-2(1H)-yl)-2-oxoethyl]-1-benzofuran-2yl}-2,2-dimethylpropan-1-one Dissolve a mixture of 17 mg [2-(2,2-dimethylpropanoyl)-5-methoxy-1-benzofuran-3-yl]acetic acid from the Step B Example 1 and 18.5 mg HOBt in 1 mL dry DMF. Add 12.3 mg trans-decahydroisoquinoline followed by 23.0 mg EDC and 35 µL DIEA. This solution was heated at 40° C. for 2 hours. It was purified directly on RP-HPLC using 65-100% MeCN gradient. The fractions containing pure product were pooled and lyophilized to give the title compound. LC-MS: 4.34 min. (m/Z=412.3, 328.2, 434.2).

EXAMPLE 11

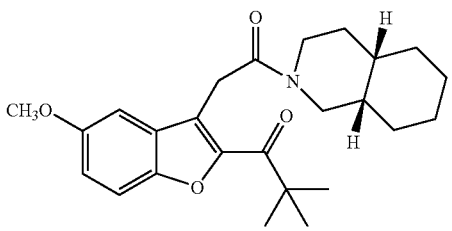

1-{5-Methoxy-3-[2-(cis-octahydroisoquinolin-2(1H)-yl)-2-oxoethyl]-1-benzofuran-2-yl}-2,2-dimethylpropan-1-one Dissolve a mixture of 17 mg [2-(2,2-dimethylpropanoyl)-5-methoxy-1-benzofuran-3-yl]acetic acid from the Step B Example 1 and 18.5 mg HOBt in 1 mL dry DMF. Add 12.3 mg cis-decahydroisoquinoline followed by 23.0 mg EDC and 35 µL DIEA. This solution was heated at 40° C. for 2 hours. It was purified directly on RP-HPLC using 65-100% MeCN gradient. The fractions containing pure product were pooled and lyophilized to give the title compound. LC-MS: 4.41 min. (m/Z=412.3, 328.2, 434.2).

EXAMPLE 12

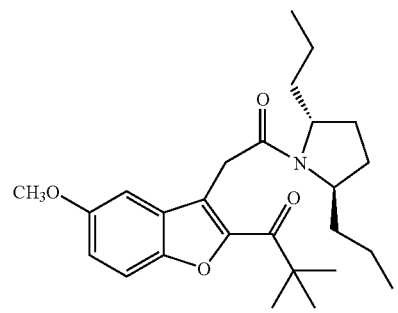

1-(3-{2-[Trans-2,5-dipropylpyrrolidin-1-yl]-2-oxoethyl}-5-methoxy-1-benzofuran-2-yl)-2,2-dimethylpropan-1-one Step A: N,N'-Dimethoxy-N,N'-dimethylsuccinamide Dissolve 136.2 g of succinyl dichloride and 180.0 g N,O-dimethylhydroxylamine hydrochloride in 1.2 L dichloromethane and cool it in an ice bath. Add 305.9 g pyridine from an addition funnel with stir over 1.5 hours. Let the reaction mixture warm up to room temperature over night. Pour the reaction mixture into ice and water and separate the layers. Wash the organic layer with cold 2 N HCl (2×), water, 5% NaHCO$_3$ (2×), and saturated brine. Dry over anhydrous Na$_2$SO$_4$ and evaporate to give crude product. It was washed with 3:1 hexanes and dichloromethane and dried to give the title compound as a light tan solid. $^1$H NMR (CDCl$_3$, 500 MHz) δ: 3.70 (s, 6H), 3.15 (s, 6H), 2.74 (s, 4H).

Step B: Decane-4,7-dione

Cool a suspension of 20.42 g N,N'-dimethoxy-N,N'-dimethylsuccinamide from the Step A above in 1 L anhydrous ether in an ice bath under nitrogen. Add 300 mL of 2 M propylmagnesium chloride in ether over 15 minutes with mechanical stir. Continue to stir the reaction mixture in the cooling bath for 2.25 hours. Quench the reaction by adding 30 mL ethanol in 50 mL ether over 30 minutes. Pour the resulting suspension into 1 L ice and water containing 75 mL concentrated HCl. Separate the layers, wash the organic layer with dilute HCl, 5% NaHCO$_3$ and saturated brine. Dry over anhydrous Na$_2$SO$_4$. Evaporate the clear yellowish solution to give the title compound as yellow solid. ¹H NMR (CDCl₃, 500 MHz) δ: 2.69 (s, 4H), 2.46 (t, J=7.4 Hz, 4H), 1.60~1.67 (m, 4H), 0.935 (t, J=7.5 Hz, 6H).

Step C: Cis- and trans-1-benzyl-2,5-dipropylpyrrolidine

Dissolve 11.92 g decane-4,7-dione from the Step B above in 4.62 g acetic acid and 100 mL methanol. Add 1.16 g potassium hydroxide pellets. Stir to dissolve the potassium hydroxide. Cool the reaction mixture in an ice acetone bath at −15° C. Add 7.50 g benzylamine followed immediately with 5.4 g sodium cyanoborohydride in several portions. Let the reaction mixture warm up to room temperature over two days. Add 45 mL 4 N HCl drop-wise and stir for 30 minutes. Evaporate the reaction mixture under reduced pressure to remove most of the solvents. Dilute the residue with water, filter off some white solid, and extract the aqueous layer with ether. This ether solution contained 2,5-dipropylpyrrole. Cool the aqueous layer with an ice bath and add solid sodium hydroxide in small portions with stir until pH ~13. Dissolve the white solid above in this mixture. Extract with ether several times. Wash the combined ether solution with saturated brine, dry over anhydrous Na₂SO₄ and evaporate to give the crude 1-benzyl-2,5-dipropylpyrrolidine. The cis and trans isomers were separated on silica gel (5~10% EtOAc in hexanes with 1% Et₃N). The fast eluting isomer was trans-1-benzyl-2,5-dipropylpyrrolidine. ¹H NMR (CDCl₃, 500 MHz) δ 7.38 (d, J=7.6 Hz, 2H), 7.29~7.33 (m, 2H), 7.21~7.24 (m, 1H), 3.83 (d, J=13.9 Hz, 1H), 3.66 (d, J=14.0 Hz, 1H), 2.86 (br s, 2H), 1.85~1.94 (m, 2H), 1.45~1.60 (m, 4H), 1.27~1.37 (m, 2H), 1.09~1.20 (m, 4H), 0.875 (t, J=7.2 Hz, 6H). The slower-eluting isomer was cis-1-benzyl-2,5-dipropylpyrrolidine. ¹H NMR (CDCl₃, 500 MHz) δ7.29~7.35 (m, 4H), 7.24~7.26 (m, 1H), 3.77 (s, 2H), 2.53~2.58 (m, 2H), 1.77~1.84 (m, 2H), 1.52~1.58 (m, 2H), 1.27~1.44 (m, 4H), 1.13~1.25 (m, 4H), 0.865 (t, J=7.2 Hz, 6H).

Step D: Trans-2,5-dipropylpyrrolidine

Dissolve 1.56 g trans-1-benzyl-2,5-dipropylpyrrolidine from the Step C above in 100 mL methanol and add 4.01 g ammonium formate and 156 mg Pd(OH)₂/C. Let the reaction mixture stir under nitrogen over night. Filter the reaction mixture through Celite to remove the catalyst. Concentrate the filtrate under reduced pressure to give a white solid residue. Suspend it in a small amount of water, add 5 mL 5 N NaOH solution, extract with ether several times, wash the combined ether solution with saturated brine, dry over anhydrous Na₂SO₄, and evaporate to give the title compound as yellow liquid. ¹H NMR (CDCl₃, 500 MHz) δ3.11~3.16 (m, 2H), 1.91~1.98 (m, 2H), 1.26~1.50 (m, 10H), 0.93 (t, J=7.1 Hz, 6H). LC-MS: 1.89 min. (M+H=156.1).

Step E: 1-(3-{2-[Trans-2,5-dipropylpyrrolidin-1-yl]-2-oxoethyl}-5-methoxy-1-benzofuran-2-yl)-2,2-dimethylpropan-1-one Dissolve a mixture of 17 mg [2-(2,2-dimethylpropanoyl)-5-methoxy-1-benzofuran-3-yl]acetic acid from the Step B Example 1 and 18.5 mg HOBt in 1 mL dry DMF. Add 13.7 mg trans-2,5-dipropylpyrrolidine from the Step D above followed by 23.0 mg EDC and 35 μL DIEA. This solution was heated at 40° C. for 2 hours. It was purified directly on RP-HPLC using 70-100% MeCN gradient. The fractions containing pure product were pooled and lyophilized to give the title compound. LC-MS: 4.58 min. (m/Z 428.3, 344.2, 450.3).

EXAMPLE 13

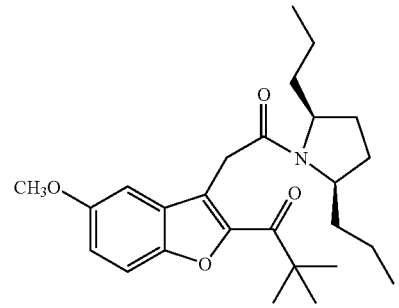

1-(3-{2-[Cis-2,5-diproplpyrrolidin-1-yl]-2-oxoethyl}-5-methoxy-1-benzofuran-2-yl)-2,2-dimethylpropan-1-one Step A: Cis-2,5-dipropylpyrrolidine The title compound was prepared in the same manner from cis-1-benzyl-2,5-dipropylpyrrolidine from Step C Example 12 using the procedure in Step D Example 12. ¹H NMR (CDCl₃, 500 MHz) δ2.94~3.00 (m, 2H), 1.81~1.89 (m, 2H), 1.25~1.54 (m, 10H), 0.94 (t, J=7.2 Hz, 6H). LC-MS: 1.83 min. (M+H=156.1).

Step B: 1-(3-{2-[Cis-2,5-dipropylpyrrolidin-1-yl]-2-oxoethyl}-5-methoxy-1-benzofuran-2-yl)-2,2-dimethylpropan-1-one Dissolve a mixture of 17 mg [2-(2,2-dimethylpropanoyl)-5-methoxy-1-benzofuran-3-yl]acetic acid from the Step B Example 1 and 18.5 mg HOBt in 1 mL dry DMF. Add 13.7 mg cis-2,5-dipropylpyrrolidine from the Step A above followed by 23.0 mg EDC and 35 μL DIEA. This solution was heated at 40° C. for 2 hours. It was purified directly on RP-HPLC using 70-100% MeCN gradient. The fractions containing pure product were pooled and lyophilized to give the title compound. LC-MS: 4.59 min. (m/Z=428.3, 344.2, 450.3).

EXAMPLE 14

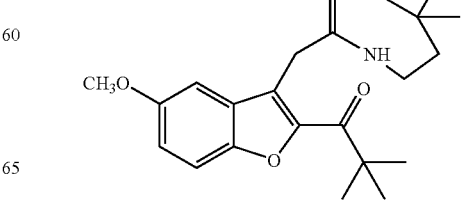

N-(3,3-Dimethylbutyl)-2-[2-(2,2-dimethylpropanoyl)-5-methoxy-1-benzofuran-3-yl]acetamide To a mixture of 29 mg [2-(2,2-dimethylpropanoyl)-5-methoxy-1-benzofuran-3-yl]acetic acid from the Step B Example 1, 23 mg HOBt, and 38.3 mg EDC was added 1 mL dry DMF. Add 24.9 mg (3,3-dimethylbutyl)amine hydrochloride followed by 61 μL DIEA. This solution was heated at 45° C. for 2 hours. It was purified directly on RP-HPLC using 60-75% MeCN gradient. The fractions containing pure product were pooled and lyophilized to give the title compound. LC-MS: 4.08 min. (m/Z=290.1, 374.2, 396.2).

EXAMPLE 15

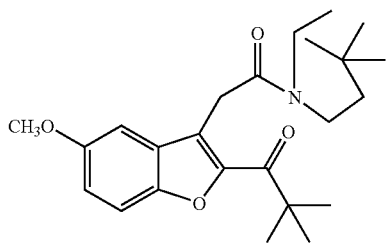

N-(3,3-Dimethylbutyl)-2-[2-(2,2-dimethylpropanoyl)-5-methoxy-1-benzofuran-3-yl]-N-ethylacetamide Step A: N-Ethyl-3,3-dimethylbutan-1-amine hydrochloride The title compound was prepared from commercially available ethylamine and 3,3-dimethylbutyraldehyde using sodium triacetoxyborohydride (Abdel-Magid, et al. J. Org. Chem. 1996, 61, 3849). $^1$H NMR (CD$_3$OD, 500 MHz) δ 3.07 (q, 7.1 Hz, 2H), 2.97~3.02 (m, 2H), 1.57~1.62 (m, 2H), 1.32 (t, 7.2 Hz, 3H), 0.98 (s, 9H).

Step B: 1-tert-butyl-6-methoxy-3H-pyrano[3,4-b][1]benzofuran-3-one

Dissolve 98 mg [2-(2,2-dimethylpropanoyl)-5-methoxy-1-benzofuran-3-yl]acetic acid from the Step B Example 1, 176 μL DIEA, and 114 mg HOBt in 3.5 mL dry DMF. Add 97.1 mg EDC and let the mixture stir at room temperature over night. It was purified directly on RP-HPLC using 50-70% MeCN gradient. The fractions containing pure product were pooled and lyophilized to give the title compound as yellow solid. $^1$H NMR (CDCl$_3$, 500 MHz) δ7.34 (dd, J=1.3 & 8.4 Hz, 1H), 7.25~7.29 (m, 2H), 6.54 (s, 1H), 3.92 (s, 3H), 1.52 (s, 9H). LC-MS: 3.55 min. (M+H=273.1).

Step C: N-(3,3-dimethylbutyl)-2-[2-(2,2-dimethylpropanoyl)-5-methoxy-1-benzofuran-3-yl]-N-ethylacetamide To a mixture containing 21.8 mg 1-tert-butyl-6-methoxy-3H-pyrano[3,4-b][1]benzofuran-3-one from the Step B above and 21.6 mg N-Ethyl-3,3-dimethylbutan-1-amine hydrochloride from the Step A above in 0.75 mL DMF was 26 μL DIEA. The mixture was heated in 45° C. oil bath over night. It was purified directly on RP-HPLC using 65~85% MeCN gradient. The fractions containing pure product were pooled and lyophilized to give the title compound. LC-MS: 4.38 min. (m/Z=318.2, 402.3, 424.3). Alternative preparation of N-(3,3-dimethylbutyl)-2-[2-(2,2-dimethylpropanoyl)-5-methoxy-1-benzofuran-3-yl]-N-ethylacetamide To a mixture of 7.7 mg [2-(2,2-dimethylpropanoyl)-5-methoxy-1-benzofuran-3-yl]acetic acid from the Step B Example 1, 6.1 mg HOBt, and 10.2 mg EDC was added 0.5 mL dry DMF. Add 6.6 N-ethyl-3,3-dimethylbutan-1-amine hydrochloride from the Step A above followed by 16 μL DIEA. This solution was heated at 45° C. over night. It was purified directly on RP-HPLC using 65-80% MeCN gradient. The fractions containing pure product were pooled and lyophilized to give the title compound. LC-MS: 4.38 min. (m/Z=424.3, 318.2, 402.3).

EXAMPLE 16

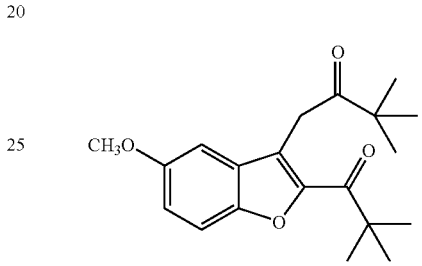

1-[2-(2,2-Dimethylpropanoyl)-5-methoxy-1-benzofuran-3-yl]-3,3-dimethylbutan-2-one Step A: 1-[3-(2-Hydroxy-3,3-dimethylbutyl)-5-methoxy-1-benzofuran-2-yl]-2,2-dimethylpropan-1-one To a solution of 0.23 g 1-(5-methoxy-3-methyl-1-benzofuran-2-yl)-2,2-dimethylpropan-1-one from Step A Example 1 in 10 mL anhydrous THF at −78° C. under nitrogen was added 0.93 mL 2 M LDA in heptane, THF, and ethylbenzene. After 15 minutes, 0.160 g trimethylacetaldehyde was added. Remove the cooling bath and let the reaction mixture warm up to room temperature. After 30 minutes, evaporate the reaction mixture under reduced pressure to remove solvents. Dilute the residue with ether, wash with 1 M HCl (2×) and saturated brine, dry over anhydrous Na$_2$SO$_4$, and evaporate to give a crude product. It was purified on RP-HPLC using 75~100% MeCN in water without TFA to give the title compound as colorless solid after lyophilization. $^1$H NMR (CDCl$_3$, 500 MHz) δ7.44 (d, J=9.2 Hz, 1H), 7.12 (dd, J=2.7 & 9.1 Hz, 1H), 7.02 (d, J=2.5 Hz, 1H), 3.89 (s, 3H), 3.48~3.52 (br m, 1H), 3.40 (br d, J=7.0 Hz, 1OH), 3.10~3.16 (m, 2H), 1.43 (s, 9H), 1.10 (s, 9H). LC-MS: 4.23 min. (m/Z=245.2, 315.2, 355.2=M+Na, 259.1). A faster-eluting isomeric side-product was also isolated during purification: 1-[2-(1-hydroxy-2,2-dimethylpropyl)-5-methoxy-1-benzofuran-3-yl]-3,3-dimethylbutan-2-one. $^1$H NMR (CDCl$_3$, 500 MHz) δ7.34 (d, J=8.9 Hz, 1H), 6.87 (dd, J=2.5 & 9.0 Hz, 1H), 6.79 (d, J=2.5 Hz, 1H), 4.53 (s, 1H), 3.99 (d, J=17.6 Hz, 1H), 3.92 (d, J=17.4 Hz, 1H), 3.84 (s, 3H), 1.32 (s, 9H), 1.06 (s, 9H). LC-MS: 3.77 min. (m/Z=355.2=M+Na, 315.2). The structures of the isomers were further confirmed by COSY and NOESY spectroscopy.

Step B: 1-[2-(2,2-Dimethylpropanoyl)-5-methoxy-1-benzofuran-3-yl]-3,3-dimethylbutan-2-one Cool 1.5 mL dichloromethane in dry ice bath under nitrogen. Add 38 mg oxalyl chloride followed by 47 mg DMSO. Stir for 30 minutes. Add a solution of 49.9 mg 1-[3-(2-hydroxy-3,3-dimethylbutyl)-5-methoxy-1-benzofuran-2-yl]-2,2-dimethylpropan-1-one from the Step A above in 2.5 mL dichloromethane. After another 25 minutes, 167 µL triethylamine were added. After stirring for additional 25 minutes, the reaction mixture was removed from the cooling bath and allowed to warm to room temperature. After 2 hours, solvents were removed under reduced pressure and the residue was purified directly on RP-HPLC using 70-100% MeCN gradient. The fractions containing pure product were pooled and lyophilized to give the title compound. $^1$H NMR (CDCl$_3$, 500 MHz) δ7.43 (d, J=8.9 Hz, 1H), 7.10 (dd, J=2.5 & 8.9 Hz, 1H), 6.90 (d, J=2.6 Hz, 1H), 4.39 (s, 2H), 3.87 (s, 3H), 1.42 (s, 9H), 1.34 (s, 9H). LC-MS: 4.17 min. (m/Z=247.2, 353.3, 331.4).

EXAMPLE 17

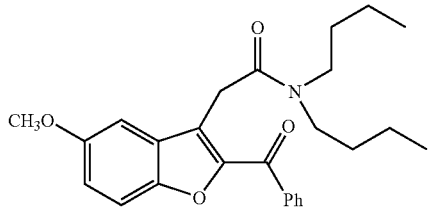

2-(2-Benzoyl-5-methoxy-1-benzofuran-3-yl)-N,N-dibutylacetamide

Step A: (5-Methoxy-3-methyl-1-benzofuran-2-yl)(phenyl)methanone

The title compound was prepared from 1-2-hydroxy-5-methoxyphenyl)ethanone, 2-bromoacetophenone, and cesium carbonate using the procedure described in Step A, Example 1. $^1$H NMR (CDCl$_3$, 500 MHz) δ 8.03~8.07 (m, 2H), 7.55~7.59 (m, 1H), 7.47~7.51 (m, 2H), 7.40 (d, J=9.0 Hz, 1H), 7.08 (dd, J=2.6 & 9.0 Hz, 1H), 7.03 (d, J=2.5 Hz, 1H), 3.86 (s, 3H), 2.59 (s, 3H). LC-MS: 3.83 min. (M+H=267.2)

Step B: (2-Benzoyl-5-methoxy-1-benzofuran-3-yl)acetic acid

The title compound was prepared from (5-methoxy-3-methyl-1-benzofuran-2-yl)(phenyl)methanone from the Step A above using procedure in Step B Example 1. The crude acidic fraction was further purified on RP-HPLC using 40~75% MeCN gradient. The fractions containing pure product were pooled and lyophilized to give the title compound. $^1$H NMR (CDCl$_3$, 500 MHz) δ 8.22~8.24 (m, 2H), 7.69~7.73 (m, 1H), 7.58~7.62 (m, 2H), 7.51 (d, J=8.9 Hz, 1H), 7.21 (dd, J=2.5 & 8.9 Hz, 1H), 7.18 (d, J=2.3 Hz, 1H), 4.17 (s, 2H), 3.93 (s, 3H). LC-MS: 3.26 min. (m/Z=265.2, 293.2).

Step C: 2-(2-Benzoyl-5-methoxy-1-benzofuran-3-yl)-N,N-dibutylacetamide

To a mixture of 10.6 mg (2-benzoyl-5-methoxy-1-benzofuran-3-yl)acetic acid from the Step B above, 7.8 mg HOBt and 13.1 mg EDC were added 6.6 mg dibutylamine and 0.5 mL DMF followed by 21 µL DIEA. After stirring at room temperature over night, it was heated in a 55° C. oil bath for 8 hours. It was purified directly on RP-HPLC using 60-95% MeCN gradient. The fractions containing pure product were pooled and lyophilized to give the title compound. $^1$H NMR (CDCl$_3$, 500 MHz) δ8.10~8.13 (m, 2H), 7.62~7.66 (m, 1H), 7.53~7.57 (m, 2H), 7.45 (d, J=8.9 Hz, 1H), 7.275 (d, J=2.7 Hz, 1H), 7.14 (dd, J=2.7 & 9.1 Hz, 1H), 4.39 (s, 2H), 3.89 (s, 3H), 3.43~3.47 (m, 2H), 3.37~3.40 (m, 2H), 1.51~1.61 (m, 4H), 1.26~1.38 (m, 4H), 0.94 (t, J=7.3 Hz, 3H), 0.90 (t, J=7.3 Hz, 3H). LC-MS: 4.24 min. (m/Z=422.3, 444.3).

EXAMPLE 18

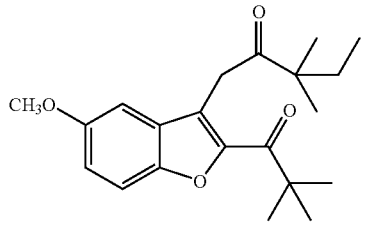

1-[2-(2,2-Dimethylpropanoyl)-5-methoxy-1-benzofuran-3-yl]-3,3-dimethylpentan-2-one

Step A: 1-[3-(2-Hydroxy-3,3-dimethylpentyl)-5-methoxy-1-benzofuran-2-yl]-2,2-dimethylpropan-1-one To a solution of 0.493 g 1-(5-methoxy-3-methyl-1-benzofuran-2-yl)-2,2-dimethylpropan-1-one from Step A Example 1 in 20 mL anhydrous THF at −78° C. under nitrogen was added 2.0 mL 2 M LDA in heptane, THF, and ethylbenzene. After 50 minutes, 0.40 g 2,2-dimethylbutanal was added. Remove the cooling bath and let the reaction mixture warm up to room temperature. After 70 minutes, the reaction was quenched by adding 2 mL saturated ammonium chloride and the reaction mixture was evaporated under reduced pressure to remove solvents. Dilute the residue with ether, wash with 1 M HCl (2×) and saturated brine, dry over anhydrous Na$_2$SO$_4$, and evaporate to give a crude product. It was purified on RP-HPLC using 65~100% MeCN in water without TFA to give the title compound as colorless solid after lyophilization. $^1$H NMR (CDCl$_3$, 500 MHz) δ7.44 (d, 9.1 Hz, 1H), 7.20 (d, 2.0 Hz, 1H), 7.10 (dd, 2.5 & 9.1 Hz, 1H), 3.86 (s, 3H), 3.58 (dd, 1.6 & 10.6 Hz, 1H), 3.29~3.34 (m, 1H), 2.90~2.95 (m, 1H), 1.51~1.59 (m, 1H), 1.39~1.46 (m, 1H), 1.40 (s, 9H), 1.02 (s, 3H), 1.01 (s, 3H), 0.92 (t, 7.6 Hz, 3H). LC-MS: 4.47 min. (m/Z=329.3, 369.2, 347). A faster-eluting isomeric side-product was also isolated during purification and was identified as 1-[2-(1-hydroxy-2,2-dimethylpropyl)-5-methoxy-1-benzofuran-3-yl]-3,3-dimethylpentan-2-one. $^1$H NMR (CDCl$_3$, 500 MHz) δ7.30 (d, 9.0 Hz, 1H), 6.84 (dd, 2.5 & 8.9 Hz, 1H), 6.75 (d, 2.5 Hz, 1H), 4.44 (s, 1H), 4.07 (AB d, 18.5 Hz, 1H), 4.04 (AB d, 18.5 Hz, 1H), 3.78 (s, 3H). 1.74 (q, 7.6 Hz, 2H), 1.263 (s, 3H), 1.260 (s, 3H), 0.99 (s, 9H), 0.91 (t, 7.4 Hz, 3H). LC-MS: 3.95 min. (m/Z=369.3=M+Na, 329.3,).

Step B: 1-[2-(2,2-Dimethylpropanoyl)-5-methoxy-1-benzofaran-3-yl]-3,3-dimethylpentan-2-one The title compounds was prepared from 1-[3-(2-hydroxy-3,3-dimethylpentyl)-5-methoxy-1-benzofuran-2-yl]-2,2-dimethylpropan-1-one from Step A above using procedure similar to that in Step B of Example 16. LC-MS: 4.36 min. (m/Z=261.2, 367.3, 345.3).

EXAMPLE 19

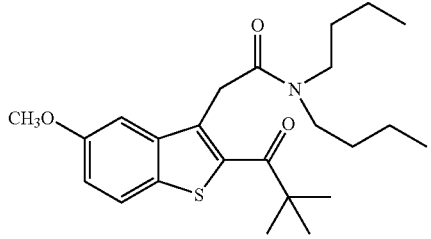

N,N-Dibutyl-2-[2-(2,2-dimethylpropanoyl)-5-methoxy-1-benzothien-3-yl]acetamide

Step A: 1-(2-Mercapto-5-methoxyphenyl)ethanone

The title compound was prepared from crude 2-mercapto-5-methoxybenzoic acid from the method of Allen and MacKay (Org. Syn. Coll Vol II, 580) using the method by Topolsiki (J. Org. Chem. 1995, 60, 5585). It was used without purification in the next step. LC-MS: 2.91 min. (m/Z=183).

Step B: 1-5-Methoxy-3-methyl-1-benzothien-2-yl)-2,2-dimethylpropan-1-one

The title compound was prepared from 1-(2-mercapto-5-methoxyphenyl)ethanone from the Step A above using the method similar to that in Step A Example 1. It was purified by recrystallization from ethyl acetate. $^1$H NMR (CDCl$_3$, 500 MHz) $\delta$7.70 (d, 8.7 Hz, 1H), 7.24 (d, 2.3 Hz, 1H), 7.135 (dd, 2.5 & 8.9 Hz, 1H), 3.93 (s, 3H), 2.56 (s, 3H), 1.41 (s, 9H). LC-MS: 4.17 min. (m/Z=221.1, 179.0, 263.1).

Step C: [2-(2,2-Dimethylpropanoyl)-5-methoxy-1-benzothien-3-yl]acetic acid

The title compound was prepared from 1-(5-methoxy-3-methyl-1-benzothien-2-yl)-2,2-dimethylpropan-1-one from Step B above using the method described in Step B Example 1. $^1$H NMR (CDCl$_3$, 500 MHz) $\delta$7.73 (d, 8.9 Hz, 1H), 7.46 (d, 2.3 Hz, 1H), 7.21 (dd, 2.6 & 9.0 Hz, 1H), 4.01 (s, 2H), 3.95 (s, 3H), 1.47 (s, 9H). LC-MS: 3.48 min. (m/Z=261.1, 289.1, 329.1, 307).

Step D: 1-tert-Butyl-6-methoxy-3H-[1]benzothieno[2,3-c]pyran-3-one

A round bottom flask was charged with 0.460 g [2-(2,2-dimethylpropanoyl)-5-methoxy-1-benzothien-3-yl]acetic acid from the Step C above, 0.345 g HOBt hydrate, and 0.504 g EDC HCl salt. This mixture was dissolved in 15 mL anhydrous DMF and 0.582 g DIEA was added. The mixture turned bright yellow. After standing at room temperature overnight, the mixture was poured into water and extracted with ether several times. The combined ether extract was washed with water (4×), 5% NaHCO$_3$, and saturated brine, dried over anhydrous Na$_2$SO$_4$, and evaporated to give the title compound as a bright yellow solid. $^1$H NMR (CDCl$_3$, 500 MHz) $\delta$7.49 (d, 8.7 Hz, 1H), 7.35 (d, 2.5 Hz, 1H), 7.20 (dd, 2.5 & 8.9 Hz, 1H), 6.65 (s, 1H), 3.92 (s, 3H), 1.51 (s, 9H). LC-MS: 3.77 min. (m/Z=289.3).

Step E: N,N-Dibutyl-2-[2-(2,2-dimethylpropanoyl)-5-methoxy-1-benzothien-3-yl]acetamide A solution of 21.6 mg of 1-tert-butyl-6-methoxy-3H-[1]benzothieno[2,3-c]pyran-3-one from the Step D above and 29.1 mg di-n-butyl amine in 0.75 mL anhydrous DMF was heated at 70° C. for six hours. The reaction mixture was purified on RP-HPLC using 70~100% MeCN gradient with 0.1% TFA. The product fractions were pooled and lyophilized to give the title compound as a white solid. LC-MS: 4.53 min. (m/Z=418.3, 440.2).

EXAMPLES 20~32

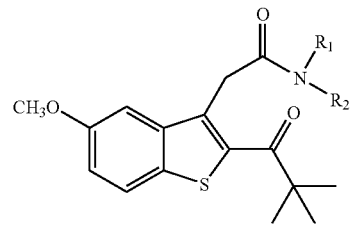

Examples 20~32 in Table 1 were prepared from 1-tert-butyl-6-methoxy-3H-[1]benzothieno[2,3-c]pyran-3-one from the Step D of Example 19 and either three equivalents of an appropriate amine or two equivalents of an appropriate amine plus two equivalents of DIEA under the conditions described in Step E of Example 19. In Example 32, an amine HCl salt was used with the doubled amount of DIEA. The preparation of amines for Examples 30~32 were described in US2003/034959 filed Nov. 4, 2003, incorporated herein by reference in its entirety.

TABLE 1

Examples 20~32

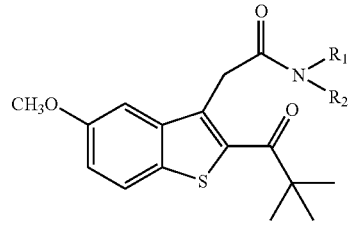

| Example | R$_1$ | R$_2$ | LC-MS t$_r$, min. | m/Z |
|---|---|---|---|---|
| 20 | i-Bu | i-Bu | 4.53 | 418.3, 440.2 |
| 21 | cyclopropylmethyl | n-Pr | 4.25 | 402.3, 424.2 |
| 22 | cyclohexyl | Et | 4.43 | 416.3, 438 |
| 23 | n-Pr | n-Pr | 4.24 | 390.3, 412.2 |
| 24 | n-Bu | Et | 4.24 | 390.3, 412.2 |
| 25 | i-Amyl | Et | 4.38 | 404.3, 426 |

TABLE 1-continued

Examples 20~32

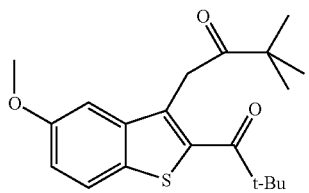

| Example | R₁ | R₂ | LC-MS t$_r$, min. | m/Z |
|---|---|---|---|---|
| 26 | n-Bu | n-Pr | 4.39 | 404.3, 426.2 |
| 27 | i-Amyl | i-Amyl | 4.76 | 446.2, 468.3 |
| 28 | H | Trans-decalinyl | 4.49 | 428.3, 450.2 |
| 29 | H | Cis-decalinyl | 4.45 | 428.4, 450.2 |
| 30 | n-Pr | Trans-cyclopentyl-n-Pr | 4.66 | 444.4, 466.3 |
| 31 | n-Pr | Cis-cyclopentyl-n-Pr | 4.69 | 444.4, 466.2 |
| 32 | 3,3-Dimethylbutyl | Et | 4.48 | 418.3, 440 |

EXAMPLE 33

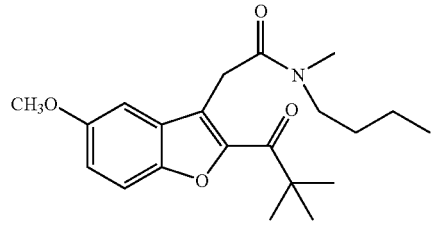

1-[2-(2,2-Dimethylpropanoyl)-5-methoxy-1-benzothien-3-yl]-3,3-dimethylbutan-2-one Step A. 1-[3-(2-Hydroxy-3,3-dimethylbutyl)-5-methoxy-1-benzothien-2-yl]-2,2-dimethylpropan-1-one The title compound was prepared from 1-(5-methoxy-3-methyl-1-benzothien-2-yl)-2,2-dimethylpropan-1-one (Step B, Example 19) using the procedure descried in Step A, Example 18. The products were isolated using RP-HPLC employing a 65~100% MeCN gradient without TFA. The title compound was isolated as the major product as a white solid after lyophilization. ¹H NMR (CD₃OD, 500 MHz) $\delta$7.65 (d, 8.7 Hz, 1H), 7.12 (d, 2.3 Hz, 1H), 6.94 (dd, 2.5 & 8.7 Hz, 1H), 4.62 (dd, 2.3 & 2.5 Hz, 1H), 3.87 (s, 3H), 3.00 (dd, 3.0 & 16.0 Hz, 1H), 2.985 (dd, 2.0 & 16.0 Hz, 1H), 1.14 (s, 9H), 1.12 (s, 9H). LC-MS: 4.54 min. (m/Z=331.2). A faster-eluting isomer was also isolated. It as identified as 1-[2-(1-hydroxy-2,2-dimethylpropyl)-5-methoxy-1-benzothien-3-yl]-3,3-dimethylbutan-2-one. Its ¹H NMR (CD₃OD, 500 MHz) $\delta$7.65 (d, 8.7 Hz, 1H), 6.94 (dd, 2.5 & 8.7 Hz, 1H), 6.83 (d, 2.5 Hz, 1H), 4.68 (s, 1H), 4.27 (d, 18.8 Hz, 1H), 4.16 (d, 18.8 Hz, 1H), 3.79 (s, 3H), 1.33 (s, 9H), 1.01 (s, 9H). LC-MS: 3.91 min. (m/Z=371.1). Unlike the cases in Examples 16 and 18, the two isomers in the current Example appeared to interconvert under ambient temperature and neutral pH spontaneously.

Step B. 1-[2-(2,2-Dimethylpropanoyl)-5-methoxy-1-benzothien-3-yl]-3,3-dimethylbutan-2-one The title compound was prepared from 1-[3-(2-hydroxy-3,3-dimethylbutyl)-5-methoxy-1-benzothien-2-yl]-2,2-dimethylpropan-1-one from the Step A above using the procedure in Step B, Example 18. It was isolated as a white solid following RP-HPLC purification (70~100% MeCN) and lyophilization. ¹H NMR (CDCl₃, 500 MHz) $\delta$7.72 (d, 8.9 Hz, 1H), 7.13 (dd, 2.4 & 8.8 Hz, 1H), 7.03 (d, 2.6 Hz, 1H), 4.40 (s, 2H), 3.88 (s, 3H), 1.41 (s, 9H), 1.35 (s, 9H). LC-MS: 4.27 min. (m/Z=369.2, 263.2, 347.3).

EXAMPLE 34

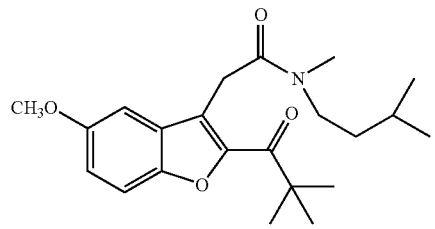

N-Butyl-2-[2-(2,2-dimethylpropanoyl)-5-methoxy-1-benzofaran-3-yl]-N-methylacetamide The title compound was prepared from 1-tert-butyl-6-methoxy-3H-pyrano[3,4-b][1]benzofuran-3-one and butyl methyl amine using the procedure from Step C Example 15. LC-MS: 3.97 min. (m/Z=360.4, 382.3, 276.2, 273.2).

EXAMPLE 35

2-[2-(2,2-Dimethylpropanoyl)-5-methoxy-1-benzofuran-3-yl]-N-methyl-N-(3-methylbutyl)acetamide The title compound was prepared from 1-tert-butyl-6-methoxy-3H-pyrano[3,4-b][1]benzofuran-3-one and i-amyl methyl amine using the procedure from Step C Example 15. LC-MS: 4.11 min. (m/Z=374.4, 396.3, 290.3, 273.2).

EXAMPLES 36~49

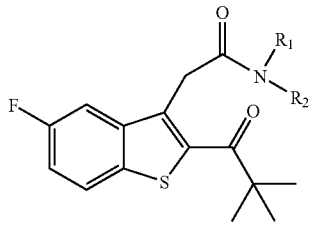

Step A. 1-(5-Fluoro-2-mercaptophenyl)ethanone

The title compound was prepared from commercially available 5-fluoro-2-mercaptobenzoic acid using the method of Topolski (J. Org. Chem. 1995, 60, 5585). It was purified using SGC with 15~25% EtOAc in hexanes. $^1$H NMR (CDCl$_3$, 500 MHz) δ7.58 (dd, $J_{H-H}$=2.8 Hz, $J_{H-F}$=9.2 Hz, 1H), 7.31 (dd, $J_{H-H}$=8.7 Hz, $J_{H-F}$=5.3 Hz, 1H), 7.12 (ddd, $J_{H-H}$=8.7 & 2.8 Hz, $J_{H-F}$=7.6 Hz, 1H), 4.49 (s, 1 SH), 2.64 (s, 3H).

Step B. 1-(5-Fluoro-3-methyl-1-benzothien-2-yl)-2,2-dimethylpropan-1-one

To a solution of 5.20 g 1-(5-fluoro-2-mercaptophenyl)ethanone in 100 mL anhydrous DMF was added 5.47 g 1-bromopinacolone and 10.95 g cesium carbonate. The resulting mixture was stirred at room temperature overnight and then heated at 70° C. for 3 days. After diluting the reaction mixture with ice and water, it was extracted with ether several times. The combined ether extract was washed with 0.05 N NaOH (2×), water (3×), and saturated brine, dried over anhydrous Na$_2$SO$_4$, and evaporated to give the crude product. The latter was purified by SGC using 10~15% EtOAc in hexanes to give the title compound as an oil. $^1$H NMR (CDCl$_3$, 500 MHz) δ7.77 (dd, $J_{H-H}$=8.7 Hz, $J_{H-F}$=4.8 Hz, 1H), 7.49 (dd, $J_{H-H}$=2.5 Hz, $J_{H-F}$=9.6 Hz, 1H), 7.24 (ddd, $J_{H-H}$=2.5 & 8.7 Hz, $J_{H-F}$=8.7 Hz, 1H), 2.53 (s, 3H), 1.40 (s, 9H). LC-MS: 4.11 min. (m/Z=209.1, 251.1).

Step C. [2-(2,2-Dimethylpropanoyl)-5-fluoro-1-benzothien-3-yl]acetic acid

The title compound was prepared from 1-(5-fluoro-3-methyl-1-benzothien-2-yl)-2,2-dimethylpropan-1-one using the procedure described in Step B Example 1. $^1$H NMR (CDCl$_3$, 500 MHz) δ7.82 (dd, $J_{H-H}$=8.8 Hz, $J_{H-F}$=4.7 Hz, 1H), 7.72 (dd, $J_{H-H}$=2.4 Hz, $J_{H-F}$=9.3 Hz, 1H), 7.32 (ddd, $J_{H-H}$=2.5 & 8.7 Hz, $J_{H-F}$=8.7 Hz, 1H), 4.00 (s, 2H), 1.46 (s, 9H). LC-MS: 3.48 min. (m/Z=249.2, 277.2, 317.2, 295).

Step D. Examples 36~49

The title compounds were prepared from [2-(2,2-dimethylpropanoyl)-5-fluoro-1-benzothien-3-yl]acetic acid using the same procedure described in Step C Example 1 except the reaction was carried out at 70° C. for 8~20 hours.

TABLE 2

Examples 36~49

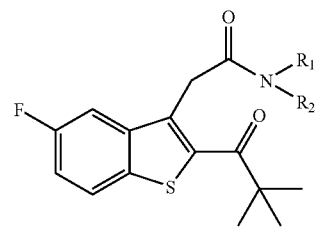

| Example | R$_1$ | R$_2$ | LC-MS t$_r$, min. | m/Z |
|---|---|---|---|---|
| 36 | n-Bu | n-Bu | 4.56 | 406.3, 428.2 |
| 37 | i-Bu | i-Bu | 4.53 | 406.3, 428 |
| 38 | cyclopropylmethyl | n-Pr | 4.27 | 390.3, 412.2 |
| 39 | cyclohexyl | Et | 4.44 | 404.3, 426 |
| 40 | n-Pr | n-Pr | 4.26 | 378.3, 400.2 |
| 41 | n-Bu | Et | 4.26 | 378.3, 400.2 |
| 42 | i-Amyl | Et | 4.40 | 392.3, 414.2 |
| 43 | n-Bu | n-Pr | 4.41 | 392.3, 414.2 |
| 44 | i-Amyl | i-Amyl | 4.78 | 434.3, 456.3 |
| 45 | Trans-decalin | | 4.49 | 416.3, 438 |
| 46 | Cis-decalin | | 4.46 | 416.3, 438 |
| 47 | Trans- n-Pr,n-Pr cyclopentane | | 4.70 | 432.3, 454.2 |
| 48 | Cis- n-Pr,n-Pr cyclopentane | | 4.77 | 432.1, 454.2 |
| 49 | 3,3-Dimethylbutyl | Et | 4.50 | 406.3, 428.2 |

EXAMPLES 50~63

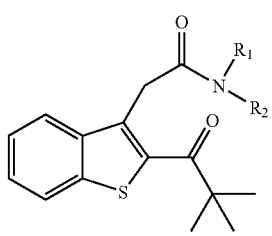

Step A. 1-(2-Mercaptophenyl)ethanone

The title compound was prepared from commercially available 2-mercaptobenzoic acid using the method of Topolski (J. Org. Chem. 1995, 60, 5585). It was purified using SGC with 15~25% EtOAc in hexanes. $^1$H NMR (CDCl$_3$, 500 MHz) $\delta$7.91 (d, 7.8 Hz, 1H), 7.33~7.35 (m, 2H), 7.21~7.25 (m, 1H), 4.51 (s, 1H), 2.66 (s, 3H). LC-MS: 2.69 min. (m/Z=59.8, 135.0, 153.0).

Step B. 2,2-Dimethyl-1-(3-methyl-1-benzothien-2-yl)propan-1-one

The title compound was prepared from 1-(2-mercaptophenyl)ethanone and 1-bromopinacolone using the procedure in Step B Examples 36~49. $^1$H NMR (CDCl$_3$, 500 MHz) $\delta$7.82~7.88 (m, 2H), 7.44~7.50 (m, 2H), 2.60 (s, 3H), 1.41 (s, 9H). LC-MS: 4.06 min. (m/Z=233.4, 191).

Step C. [2-(2,2-Dimethylpropanoyl)-1-benzothien-3-yl]acetic acid

The title compound was prepared from 2,2-dimethyl-1-(3-methyl-1-benzothien-2-yl)propan-1-one using the procedure in Step B Example 1. $^1$H NMR (CDCl$_3$, 500 MHz) $\delta$8.09 (d, 7.5 Hz, 1H), 7.88 (d, 7.1 Hz, 1H), 7.51~7.58 (m, 2H), 4.06 (s, 2H), 1.48 (s, 9H). LC-MS: 3.36 min. (m/Z=231.1, 259.1, 299.1, 277).

Step D. 1-tert-Butyl-3H-[1]benzothieno[2,3-c]pyran-3-one

The title compound was prepared from [2-(2,2-dimethylpropanoyl)-1-benzothien-3-yl]acetic acid using the procedure in Step D Examples 20~32. $^1$H NMR (CDCl$_3$, 500 MHz) $\delta$7.93 (d, 8.0 Hz, 1H), 7.62 (d, 8.0 Hz, 1H), 7.56~7.59 (m, 1H), 7.38~7.41 (m, 1H), 6.70 (s, 1H), 1.52 (s, 9H). LC-MS: 3.61 min. (m/Z=259.2).

Step E. Examples 50~63

Examples 50~63 in Table 3 were prepared from 1-tert-butyl-3H-[1]benzothieno[2,3-c]pyran-3-one and appropriate amine or amine HCl salt using a similar method as the one described in Step E Example 19.

TABLE 3

Examples 50~63

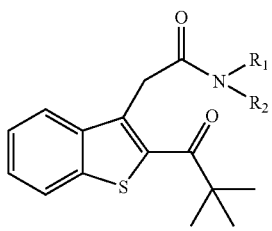

| Example | R$_1$ | R$_2$ | t$_r$, min. | LC-MS m/Z |
|---|---|---|---|---|
| 50 | n-Bu | n-Bu | 4.44 | 388.3, 410.3, 304.2, 259.1 |
| 51 | i-Bu | i-Bu | 4.41 | 388.3, 410.3, 304.2, 259.2 |

TABLE 3-continued

Examples 50~63

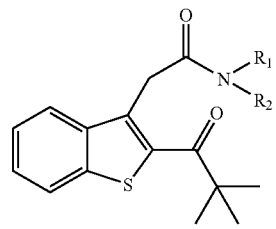

| Example | R$_1$ | R$_2$ | t$_r$, min. | LC-MS m/Z |
|---|---|---|---|---|
| 52 | cyclopropylmethyl | n-Pr | 4.15 | 372.3, 394.2, 288.2, 259.2 |
| 53 | cyclohexyl | Et | 4.32 | 386.3, 408, 259.2, 302.3 |
| 54 | n-Pr | n-Pr | 4.13 | 360.3, 276.2, 382.3, 259.2 |
| 55 | n-Bu | Et | 4.14 | 360.3, 276.2, 382.3, 259.2 |
| 56 | i-Amyl | Et | 4.66 | 416.4, 438, 332.3, 259.2 |
| 57 | n-Bu | n-Pr | 4.28 | 374.4, 290.3, 396.3, 259.2 |
| 58 | i-Amyl | i-Amyl | 4.30 | 374.4, 290.3, 396.3, 259.2 |
| 59 | Trans- (decalin) | | 4.39 | 398.3, 420.3, 314.3, 259 |
| 60 | Cis- (decalin) | | 4.35 | 398.3, 420.3, 314.3, 259 |
| 61 | Trans- n-Pr/n-Pr cyclopentyl | | 4.58 | 414.4, 436.3, 330.3, 259.2 |
| 62 | Cis- n-Pr/n-Pr cyclopentyl | | 4.61 | 414.4, 436.3, 330.3, 259.2 |
| 63 | 3,3-Dimethylbutyl | Et | 4.38 | 388.4, 410.3, 304.2, 259.2 |

Functional Assays

Maxi-K Channel

The activity of the compounds can also be quantified by the following assay.

The identification of inhibitors of the Maxi-K channel can be accomplished using Aurora Biosciences technology, and is based on the ability of expressed Maxi-K channels to set cellular resting potential after transient transfection of both α and β subunits of the channel in TsA-201 cells. In the absence of inhibitors, cells display a hyperpolarized membrane potential, negative inside, close to $E_K$ (−80 mV) which is a consequence of the activity of the Maxi-K channel. Blockade of the Maxi-K channel will cause cell depolarization. Changes in membrane potential can be determined with voltage-sensitive fluorescence resonance energy transfer (FRET) dye pairs that use two components, a donor coumarin ($CC_2DMPE$) and an acceptor oxanol ($DiSBAC_2(3)$). Oxanol is a lipophilic anion and distributes across the membrane according to membrane potential. Under normal conditions, when the inside of the cell is negative with respect to the outside, oxanol is accumulated at, the outer leaflet of the membrane and excitation of coumarin will cause FRET to occur. Conditions that lead to membrane depolarization will cause the oxanol to redistribute to the inside of the cell, and, as a consequence, to a decrease in FRET. Thus, the ratio change (donor/acceptor) increases after membrane depolarization.

Transient transfection of the Maxi-K channel in TsA-201 cells can be carried out as previously described (Hanner et al. (1998) J. Biol. Chem. 273, 16289-16296) using FUGENE6™ as the transfection reagent. Twenty four hours after transfection, cells are collected in $Ca^{2+}$-$Mg^{2+}$-free Dulbecco's phosphate-buffered saline (D-PBS), subjected to centrifugation, plated onto 96-well poly-d-lysine coated plates at a density of 60,000 cells/well, and incubated overnight. The cells are then washed 1× with D-PBS, and loaded with 100 µl of 4 µM $CC_2DMPE$-0.02% pluronic-127 in D-PBS. Cells are incubated at room temperature for 30 min in the dark. Afterwards, cells are washed 2× with D-PBS and loaded with 100 µl of 6 µM $DiSBAC_2(3)$ in (mM): 140 NaCl, 0.1 KCl, 2 $CaCl_2$, 1 $MgCl_2$, 20 Hepes-NaOH, pH 7.4, 10 glucose. Test compounds are diluted into this solution, and added at the same time. Cells are incubated at room temperature for 30 min in the dark.

Plates are loaded into a voltage/ion probe reader (VIPR) instrument, and the fluorescence emission of both $CC_2DMPE$ and $DiSBAC_2(3)$ are recorded for 10 sec. At this point, 100 µl of high-potassium solution (mM): 140 KCl, 2 $CaCl_2$, 1 $MgCl_2$, 20 Hepes-KOH, pH 7.4, 10 glucose are added and the fluorescence emission of both dyes recorded for an additional 10 sec. The ratio $CC_2DMPE/DiSBAC_2(3)$, before addition of high-potassium solution equals 1. In the absence of any inhibitor, the ratio after addition of high-potassium solution varies between 1.65-2.0. When the Maxi-K channel has been completely inhibited by either a known standard or test compound, this ratio remains at 1. It is possible, therefore, to titrate the activity of a Maxi-K channel inhibitor by monitoring the concentration-dependent change in the fluorescence ratio.

The compounds of this invention were found to cause concentration-dependent inhibition of the fluorescence ratio with $IC_{50}$'s in the range of about 1nM to about 20 µM, more preferably from about 10 nM to about 500 nM.

B. Electrophysiological Assays of Compound Effects On High-conductance Calcium-activated Potassium Channels Human Non-pigmented Ciliary Epithelial Cells The activity of high-conductance calcium-activated potassium (maxi-K) channels in human non-pigmented ciliary epithelial cells was determined using electrophysiological methods. Currents through maxi-K channels were recorded in the inside-out configuration of the patch clamp technique, where the pipette solution faces the extracellular side of the channel and the bath solution faces the intracellular side. Excised patches contained one to about fifty maxi-K channels. Maxi-K channels were identified by their large single channel conductance (250-300 pS), and by sensitivity of channel gating to membrane potential and intracellular calcium concentration. Membrane currents were recorded using standard electrophysiological techniques. Glass pipettes (Garner 7052) were pulled in two stages with a Kopf puller (model 750), and electrode resistance was 1-3 megohms when filled with saline. Membrane currents were recorded with EPC9 (HEKA Instruments) or Axopatch 1D (Axon Instruments) amplifiers, and digital conversion was done with ITC-16 interfaces (Instrutech Corp). Pipettes were filled with (mM); 150 KCl, 10 Hepes, 1 $MgCl_2$, 0.01 $CaCl_2$, 3.65 KOH, pH 7.20. The bath (intracellular) solution was identical, except, in some cases, calcium was removed, 1 mM EGTA was added and 20 mM KCl was replaced with 20 mM KF to eliminate calcium to test for calcium sensitivity of channel gating. Drugs were applied to the intracellular side of the channel by bath perfusion.

Human non-pigmented ciliary epithelial cells were grown in tissue culture as described (Martin-Vasallo, P., Ghosh, S., and Coca-Prados, M., 1989, J. Cell. Physiol. 141, 243-252), and plated onto glass cover slips prior to use. High resistance seals (>1 Gohm) were formed between the pipette and cell surface, and inside out patches were excised. Maxi-K channels in the patch were identified by their gating properties; channel open probability increased in response to membrane depolarization and elevated intracellular calcium. In patches used for pharmacological analysis, removing intracellular calcium eliminated voltage-gated currents. Maxi-K currents were measured after depolarizing voltage steps or ramps that caused channel opening.

The compounds of this invention were applied to the intracellular side of the channel in appropriate concentrations (0.001 to 100 µM). The compounds reduced channel open probability, and this effect was reversed upon washout of compounds from the experimental chamber. The IC50 for block of maxi-K channels under these conditions for the compounds of this invention ranged from about 0.5 nM to about 10 µM.

What is claimed is:

1. A compound of the structural formula I:

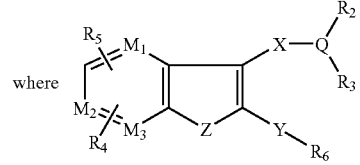

Formula I where or a pharmaceutically acceptable salt, enantiomer, diastereomer or mixture thereof:

wherein,

R represents hydrogen, or $C_{1-6}$ alkyl;

X represents —$(CHR_7)_p$—, or —$(CHR_7)_pCO$—;

Y represents —$CO(CH_2)_n$—, $(CH_2)_n$, —$CH(OR)$—, $OR_6$, or $SR_6$;

Z=O or S;

M1, M2, and M3 are independently CH or N;

Q represents, N;

RY represents H, $C_{1-6}$ alkyl, —$(CH_2)_nC_{3-8}$ cycloalkyl, —$(CH_2)_nC_{3-10}$ heterocyclyl, —$(CH_2)_nC_{5-10}$ heteroaryl, or —$(CH_2)_nC_{6-10}$ aryl;

$R_w$ represents H, $C_{1-6}$ alkyl, —$C(O)C_{1-6}$ alkyl, —$C(O)OC_{1-6}$ alkyl, —$SO_2N(R)_2$, —$SO_2C_{1-6}$ alkyl, —$SO_2C_{6-10}$ aryl, $NO_2$, CN or —$C(O)N(R)_2$;

$R_2$ represents hydrogen, $C_{1-10}$ alkyl, OH, $C_{2-6}$ alkenyl, $C_{1-6}$ alkylSR, —$(CH_2)_nO(CH_2)_mOR$, —$(CH_2)_n(CHR_7)_q(CH_2)_mC_{1-6}$ alkoxy, —$(CH_2)_n(CHR_7)_q(CH_2)_mC_{3-8}$cycloalkenyl, —(CH$_2$)$_n$(CHR$_7$)$_q$(CH$_2$)$_m$C$_{3-10}$ heterocyclyl, —N(R)$_2$, —COOR, or —(CH$_2$)$_n$(CHR$_7$)$_q$(CH$_2$)$_m$ C$_{6-10}$ aryl, said alkyl, cycloalkyl, heterocyclyl, or aryl optionally substituted with 1-5 groups selected from R$^a$;

R$_3$ represents hydrogen, C$_{-1-10}$ alkyl, C$_{2-6}$ alkenyl, —(CH$_2$)$_n$(CHR$_7$)$_q$(CH$_2$)$_m$C$_{3-8}$ cycloalkyl, —(CH$_2$)$_n$(CHR$_7$)$_q$(CH$_2$)$_m$cycloalkenyl, —(CH$_2$)$_n$(CHR$_7$)$_q$(CH$_2$)$_m$ C$_{3-10}$ heterocyclyl, —(CH$_2$)$_n$(CHR$_7$)$_q$(CH$_2$)$_m$COOR, —(CH$_2$)$_n$(CHR$_7$)$_q$(CH$_2$)$_m$C$_{6-10}$ aryl, —(CH$_2$)$_n$(CHR$_7$)$_q$(CH$_2$)$_m$NHR$_8$, —(CH$_2$)$_n$(CHR$_7$)$_q$(CH$_2$)$_m$N(R)$_2$, —(CH$_2$)$_n$(CHR$_7$)$_q$(CH$_2$)$_m$N(R)$_3$, —(CH$_2$)$_n$(CHR$_7$)$_q$(CH$_2$)$_m$N(R$_8$)$_2$, —(CH$_2$)$_n$(CHR$_7$)$_q$(CH$_2$)$_m$NHCOOR, —(CH$_2$)$_n$(CHR$_7$)$_q$(CH$_2$)$_m$N(R$_8$)CO$_2$R, —(CH$_2$)$_n$(CHR$_7$)$_q$(CH$_2$)$_m$N(R$_8$)COR, —(CH$_2$)$_n$(CHR$_7$)$_q$(CH$_2$)$_m$NHCOR, —(CH$_2$)$_n$(CHR$_7$)$_q$(CH$_2$)$_m$CONH(R$_8$), aryl, —(CH$_2$)$_n$(CHR$_7$)$_q$(CH$_2$)$_m$C$_{1-6}$alkoxy, CF$_3$, —(CH$_2$)$_n$(CHR$_7$)$_q$(CH$_2$)$_m$SO$_2$R, —(CH$_2$)$_n$(CHR$_7$)$_q$(CH$_2$)$_m$SO$_2$N(R)$_2$, —(CH$_2$)$_n$(CHR$_7$)$_q$(CH$_2$)$_m$CON(R)$_2$, —(CH$_2$)$_n$(CHR$_7$)$_q$(CH$_2$)$_m$CONHC(R)$_3$, —(CH$_2$)$_n$(CHR$_7$)$_q$(CH$_2$)$_m$ CONHC(R)$_2$CO$_2$R, —(CH$_2$)$_n$ (CHR$_7$)$_q$(CH$_2$)$_m$COR$_8$, nitro, cyano or halogen, said alkyl, cycloalkyl, alkoxy, heterocyclyl, or aryl optionally substituted with 1-5 groups of R$^a$;

R$_4$ and R$_5$ independently represent hydrogen, C$_{1-6}$ alkoxy, OH, C$_{1-6}$ alkyl, C$_{1-6}$ alkyl-S, C$_{1-6}$ alkyl-CO—, C$_{1-6}$ alkenyl, C$_{3-8}$ cycloalkoxy, C$_{3-8}$ cycloalkyl, C$_{3-8}$ cycloalkyl-S, C$_{3-8}$ cycloalkyl—CO—, COOR, SO$_3$H, —O(CH$_2$)$_n$N(R)$_2$, —O(CH$_2$)$_n$CO$_2$R, —OPO(OH)$_2$, CF$_3$, —N(R)$_2$, nitro, cyano, C$_{1-6}$ alkylamino, or halogen;

R$_6$ represents hydrogen, C$_{1-10}$ alkyl, —(CH$_2$)$_n$(CHR$_7$)$_q$(CH$_2$)$_m$C$_{6-10}$ aryl, —(CH$_2$)$_n$(CHR$_7$)$_q$(CH$_2$)$_m$C$_{5-10}$ heteroaryl, NR$_c$R$_d$, —NR—(CH$_2$)$_n$(CHR$_7$)$_q$(CH$_2$)$_m$C$_{6-10}$ aryl, —N—((CH$_2$)$_n$(CHR$_7$)$_q$(CH$_2$)$_m$C$_{6-10}$ aryl)$_2$, —(CH$_2$)$_n$(CHR$_7$)$_q$(CH$_2$)$_m$C$_{3-10}$ heterocyclyl, —NR—(CH$_2$)$_n$(CHR$_7$)$_q$(CH$_2$)$_m$C$_{3-10}$ heterocyclyl, —N—((CH$_2$)$_n$(CHR$_7$)$_q$(CH$_2$)$_m$C$_{3-10}$ heterocyclyl)$_2$ (C$_{6-10}$ aryl)O—, —(CH$_2$)$_n$(CHR$_7$)$_q$(CH$_2$)$_m$C$_{3-8}$ cycloalkyl, —COOR, —C(O)CO$_2$R, said aryl, cycloalkyl, heteroaryl, heterocyclyl and alkyl optionally substituted with 1-3 groups selected from R$^a$;

R$_c$ and R$_d$ independently represent H, C$_{1-6}$ alkyl, C$_{2-6}$ alkenyl, —(CH$_2$)$_n$C$_{6-10}$ aryl, —(CH$_2$)$_n$C$_{5-10}$ heteroaryl, C$_{1-6}$ alkylSR, —(CH$_2$)$_n$O(CH$_2$)$_m$OR, —(CH$_2$)$_n$C$_{1-6}$ alkoxy, or —(CH$_2$)$_n$C$_{3-8}$ cycloalkyl;

or R$_c$ and R$_d$ taken together with the intervening N atom form a 4-10 membered heterocyclic carbon ring optionally interrupted by 1-2 atoms of O, S, C(O) or NR, and optionally having 1-4 double bonds, and optionally substituted by 1-3 groups selected from R$^a$;

R$_7$ represents hydrogen, C$_{1-6}$ alkyl, —(CH$_2$)$_n$COOR or —(CH$_2$)$_n$N(R)$_2$, R$_8$ represents —(CH$_2$)$_n$C$_{3-8}$ cycloalkyl, —(CH$_2$)$_n$ 3-10 heterocyclyl, C$_{1-6}$ alkoxy or —(CH$_2$)$_n$C$_{5-10}$ heteroaryl, —(CH$_2$)$_n$C$_{6-10}$ aryl said cycloalkyl, aryl or heteroaryl optionally substituted with 1-3 groups selected from R$^a$;

R$^a$ represents F, Cl, Br, I, CF$_3$, N(R)$_2$, NO$_2$, CN, —COR$_8$, —CONHR$_8$, —CON(R$_8$)$_2$, —O(CH$_2$)$_n$COOR, —NH(CH$_2$)$_n$OR, —COOR, —OCF$_3$, —NHCOR, —SO$_2$R, —SO$_2$NR$_2$, —SR, (C$_1$-C$_6$ alkyl)O—, —(CH$_2$)$_n$O(CH$_2$)$_m$ OR, —(CH$_2$)$_n$C$_{1-6}$ alkoxy, (aryl)O—, —OH, (C$_1$-C$_6$ alkyl)S(O)$_m$—, H$_2$N—C(NH)—, (C$_1$-C$_6$ alkyl)C(O)—, (C$_1$-C$_6$ alkyl)OC(O)NH—, —(C$_1$-C$_6$ alkyl)NR$_w$(CH$_2$)$_n$ C$_{3-10}$ heterocyclyl-R$_w$, —(C$_1$-C$_6$ alkyl)O(CH$_2$)$_n$C$_{3-10}$ heterocyclyl-R$_w$, —(C$_1$-C$_6$ alkyl)S(CH$_2$)$_n$ C$_{3-10}$ heterocyclyl-R$_w$, —(C$_1$-C$_6$ alkyl)-C$_{3-10}$ heterocyclyl-R$_w$, —(CH$_2$)$_n$-Z$^1$—C(=Z$^2$)N(R)$_2$, —(C$_{2-6}$ alkenyl)NR$_w$(CH$_2$)$_n$C$_{3-10}$ heterocyclyl-R$_w$, —(C$_{2-6}$ alkenyl)O(CH$_2$)$_n$C$_{3-10}$ heterocyclyl-R$_w$, —C$_{2-6}$ alkenyl)S(CH$_2$)$_n$C$_{3-10}$ heterocyclyl-R$_w$, —(C$_{2-6}$ alkenyl)-C$_{3-10}$ heterocyclyl-R$_w$, —(C$_{2-6}$ alkenyl)-Z$^1$—C(=Z$^2$)N(R)$_2$, —(CH$_2$)$_n$SO$_2$R, —(CH$_2$)$_n$SO$_3$H, —(CH$_2$)$_n$PO(OR)$_2$, —(CH$_2$)$_n$OH, —(CH$_2$)$_n$(CHR$_7$)$_q$(CH$_2$)$_m$OPO(OR)$_2$, C$_{3-10}$cycloalkyl, C$_{6-10}$ aryl, C$_{3-10}$ heterocyclyl, C$_{2-6}$ alkenyl, and C$_1$-C$_{10}$ alkyl, said alkyl, alkenyl, alkoxy, heterocyclyl and aryl optionally substituted with 1-3 groups selected from C$_1$-C$_6$ alkyl, CN, NO$_2$, —(CH$_2$)$_n$OH, —(CH$_2$)$_n$OPO(OR)$_2$, CON(R)$_2$ and COOR;

Z$^1$ and Z$^2$ independently represents NR$_w$, O, CH$_2$, or S;

m is 0-3;

n is 0-3;

p is 0-3 and q is 0-1.

2. A compound according to claim 1 wherein Q is —N— and Y is —CO(CH$_2$)$_n$.

3. A compound according to claim 2 wherein n=0, Z is S, and R$_6$ is C$_{1-6}$ alkyl, (CH$_2$)$_n$C$_{6-10}$ aryl, (CH$_2$)$_n$C$_{5-10}$ heteroaryl, (CH$_2$)$_n$C$_{3-10}$ heterocyclyl, NR$_c$R$_d$ or (CH$_2$)$_n$C$_{3-8}$ cycloalkyl, said alkyl, aryl, heteroaryl, heterocyclyl and alkyl optionally substituted with 1 to 3 groups of R$^a$.

4. A compound according to claim 3 wherein M1, M2 and M3 are CH, X is —(CHR$_7$)$_p$CO—, p is 1-3, R$_2$ is C$_{1-10}$ alkyl or C$_{1-6}$ alkylOH and R$_3$ is (CH$_2$)$_n$C$_{3-10}$ heterocyclyl, said heterocyclyl and alkyl optionally substituted with 1 to 3 groups of R$^a$.

5. A compound according to claim 2 wherein n=0, Z is O, and R$_6$ is C$_{1-6}$ alkyl, (CH$_2$)$_n$C$_{6-10}$ aryl, (CH$_2$)$_n$C$_{5-10}$ heteroaryl, (CH$_2$)$_n$C$_{3-10}$ heterocyclyl, NR$_c$R$_d$ or (CH$_2$)$_n$C$_{3-8}$ cycloalkyl, said alkyl, aryl, heteroaryl, heterocyclyl and alkyl optionally substituted with 1 to 3 groups of R$^a$.

6. A compound according to claim 5 wherein M1, M2 and M3 are CH, X is —(CHR$_7$)$_p$CO—, p is 1-3, R$_2$ is C$_{1-10}$ alkyl or C$_{1-6}$ alkylOH and R$_3$ is (CH$_2$)$_n$C$_{3-10}$ heterocyclyl, said heterocyclyl and alkyl optionally substituted with 1 to 3 groups of R$^a$.

7. A compound according to claim 1 where a free hydroxyl group is present, said hydroxyl group optionally derivatized to give a phosphate group represented as —OPO(OH)$_2$.

8. A compound which is:

N,N-Bibutyl-2-[2-(2,2-dimethylpropanoyl)-5-methoxy-1-benzofuran-3-yl]acetamide,

2-[2-(2,2-Dimethylpropanoyl)-5-methoxy-1-benzofuran-3-yl]-N,N-diisobutylacetamide, 2-[2-(2,2-Dimethylpropanoyl)-5-methoxy-1-benzofuran-3-yl]-N,N-dipropylacetamide, N-Butyl-2-[2-(2,2-ethylpropanoyl)-5-methoxy-1-benzofuran-3-yl]-N-ethylacetamide, 2-[2-(2,2-Dimethylpropanoyl)-5-methoxy-1-benzofaran-3-yl]-N,N-bis(3-methylbutyl)acetamide, 2-[2-(2,2-Dimethylpropanoyl)-5-methoxy-1-benzofuran-3-yl]-N-ethyl-N-(3-methylbutyl)acetamide, N-Butyl-2-[2-(2,2-dimethylpropanoyl)-5-methoxy-1-benzofuran-3-yl]-N-propylacetamide, N-(3,3-Dimethylbutyl)-2-[2-(2,2-dimethylpropanoyl)-5-methoxy-1-benzofuran-3-yl]acetamide, N-(3,3-Dimethylbutyl)-2-[2-(2,2-ethylpropanoyl)-5-methoxy-1-benzofuran-3-yl]-N-ethylacetamide, 2-(2-Benzoyl-5-methoxy-1-benzofuran-3-yl)-N,N-dibutylacetamide, 2-[2-(2,2-dimethylpropanoyl)-5-methoxy-1-benzothien-3-yl]-N,N-di-n-butylacetamide;

2-[2-(2,2-dimethylpropanoyl)-5-methoxy-1-benzothien-3-yl]-N,N-diisobutylacetamide;

2-[2-(2,2-dimethylpropanoyl)-5-methoxy-1-benzothien-3-yl]-N,N-dipropylacetamide;
N-butyl-2-[2-(2,2-dimethylpropanoyl)-5-methoxy-1-benzothien-3-yl]-N-ethylacetamide;
2-[2-(2,2-methylpropanoyl)-5-methoxy-1-benzothien-3-yl]-N-ethyl-N-(3-methylbutyl)acetamide;
N-butyl-2-[2-(2,2-dimethylpropanoyl)-5-methoxy-1-benzothien-3-yl]-N-propylacetamide;
2-[2-(2,2-dimethylpropanoyl)-5-methoxy-1-benzothien-3-yl]-N,N-bis(3-methylbutyl)acetamide;
N-(3,3-dimethylbutyl)-2-[2-(2,2-dimethylpropanoyl)-5-methoxy-1-benzothien-3-yl]-N-ethylacetamide;
N-Butyl-2-[2-(2,2-dimethylpropanoyl)-5-methoxy-1-benzofuran-3-yl]-N-methylacetamide;
2-[2-(2,2-Dimethylpropanoyl)-5-methoxy-1-benzofuran-3-yl]-N-methyl-N-(3-methylbutyl)acetamide;
2-[2-(2,2-dimethylpropanoyl)-5-fluoro-1-benzothien-3-yl]-N,N-di-n-butylacetamide;
2-[2-(2,2-dimethylpropanoyl)-5-fluoro-1-benzothien-3-yl]-N,N-diisobutylacetamide;
2-[2-(2,2-dimethylpropanoyl)-5-fluoro-1-benzothien-3-yl]-N,N-dipropylacetamide;
N-butyl-2-[2-(2,2-dimethylpropanoyl)-5-fluoro-1-benzothien-3-yl]-N-ethylacetamide;
2-[2-(2,2-dimethylpropanoyl)-5-fluoro-1-benzothien-3-yl]-N-ethyl-N-(3-methylbutyl)acetamide;
N-butyl-2-[2-(2,2-dimethylpropanoyl)-5-fluoro-1-benzothien-3-yl]-N-propylacetamide;
2-[2-(2,2-dimethylpropanoyl)-5-fluoro-1-benzothien-3-yl]-N,N-bis(3-methylbutyl)acetamide;
N-(3,3-dimethylbutyl)-2-[2-(2,2-dimethylpropanoyl)-5-fluoro-1-benzothien-3-yl]-N-ethylacetamide;
2-[2-(2,2-dimethylpropanoyl)-1-benzothien-3-yl]-N,N-di-n-butylacetamide;
2-[2-(2,2-dimethylpropanoyl)-1-benzothien-3-yl]-N,N-diisobutylacetamide;
2-[2-(2,2-dimethylpropanoyl)-1-benzothien-3-yl]-N,N-dipropylacetamide;
N-butyl-2-[2-(2,2-dimethylpropanoyl)-1-benzothien-3-yl]-N-ethylacetamide;
2-[2-(2,2-dimethylpropanoyl)-1-benzothien-3-yl]-N-ethyl-N-(3-methylbutyl)acetamide;
N-butyl-2-[2-(2,2-dimethylpropanoyl)-1-benzothien-3-yl]-N-propylacetamide;
2-[2-(2,2-dimethylpropanoyl)-1-benzothien-3-yl]-N,N-bis(3-methylbutyl)acetamide;
N-(3,3-dimethylbutyl)-2-[2-(2,2-dimethylpropanoyl-1-benzothien-3-yl]-N-ethylacetamide;

or a pharmaceutically acceptable salt, enantiomer, diastereomer or mixture thereof.

9. A method for the treatment ocular hypertension or glaucoma comprising administering to a patient in need thereof a therapeutically effective amount of a compound of structural formula I.

10. A composition comprising a compound of formula I of claim 1 and a pharmaceutically acceptable carrier.

11. The composition according to claim 10 wherein the compound of formula I is applied as a topical formulation, said topical formulation administered as a solution or suspension and optionally contains xanthan gum or gellan gum.

12. A composition according to claim 11 wherein one or more of an active ingredient belonging to the group consisting of: β-adrenergic blocking agent, parasympatho-mimetic agent, sympathomimetic agent, carbonic anhydrase inhibitor, EP4 agonist, a prostaglandin or derivative thereof, hypotensive lipid, neuroprotectant, and/or 5-HT2 receptor agonist is optionally added.

13. A composition according to claim 12 wherein the β-adrenergic blocking agent is timolol, betaxolol, levobetaxolol, carteolol, or levobunolol; the parasympathomimetic agent is pilocarpine; the sympathomimetic agent is epinephrine, brimonidine, iopidine, clonidine, or para-aminoclonidine, the carbonic anhydrase inhibitor is dorzolamide, acetazolamide, metazolamide or brinzolamide; the prostaglandin is latanoprost, travaprost, unoprostone, rescula, or S1033, the hypotensive lipid is lumigan, the neuroprotectant is eliprodil, R-eliprodil or memantine; and the 5-HT2 receptor agonist is 1-(2-aminopropyl)-3-methyl-1H-imdazol-6-ol fumarate or 2-(3-chloro-6-methoxy-indazol-1-yl)-1-methyl-ethylamine.

* * * * *